(12) United States Patent
Rubin

(10) Patent No.: US 12,318,718 B2
(45) Date of Patent: *Jun. 3, 2025

(54) SYSTEMS AND METHODS FOR REHABILITATING ALCOHOL COMPOSITIONS AND REHABILITATED ALCOHOLIC PRODUCTS

(71) Applicant: True Essence Foods Inc., Indianapolis, IN (US)

(72) Inventor: Matthew J. Rubin, Indianapolis, IN (US)

(73) Assignee: TRUE ESSENCE FOODS INC., Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/005,696

(22) PCT Filed: Jul. 27, 2021

(86) PCT No.: PCT/US2021/043272
§ 371 (c)(1),
(2) Date: Jan. 17, 2023

(87) PCT Pub. No.: WO2022/026441
PCT Pub. Date: Feb. 3, 2022

(65) Prior Publication Data
US 2023/0271102 A1 Aug. 31, 2023

Related U.S. Application Data

(63) Continuation of application No. 16/939,340, filed on Jul. 27, 2020, now Pat. No. 11,213,766.
(Continued)

(51) Int. Cl.
B01D 3/10 (2006.01)
B01D 3/00 (2006.01)
(Continued)

(52) U.S. Cl.
CPC ............. B01D 3/106 (2013.01); B01D 3/001 (2013.01); B01D 3/42 (2013.01); C07C 29/84 (2013.01); C12F 3/06 (2013.01); C12G 3/08 (2013.01)

(58) Field of Classification Search
CPC .......... B01D 3/001; B01D 3/106; B01D 3/42; C07C 29/84; C12F 3/06; C12G 3/08
See application file for complete search history.

(56) References Cited

U.S. PATENT DOCUMENTS 4,347,321 A 8/1982 Lionelle
5,458,739 A 10/1995 Boucher
(Continued)

FOREIGN PATENT DOCUMENTS

CN 112522057 3/2021

OTHER PUBLICATIONS

Second Office Action received for Chinese Application No. 202180065204.1, dated Jul. 3, 2024, 24 pages.
(Continued)

Primary Examiner — Jonathan Miller
(74) Attorney, Agent, or Firm — QUARLES & BRADY LLP

(57) ABSTRACT

A method for removing one or more congeners from an alcoholic composition, including placing a quantity of an alcoholic composition in a pressure-controllable environment, decreasing the pressure of the pressure-controllable environment, removing one or more unwanted congeners from the alcoholic composition to yield a purified alcoholic composition, and removing the purified alcoholic composition from the pressure-controllable environment.

25 Claims, 21 Drawing Sheets

Related U.S. Application Data

(60) Provisional application No. 63/209,487, filed on Jun. 11, 2021, provisional application No. 63/156,517, filed on Mar. 4, 2021.

(51) Int. Cl.
*B01D 3/42* (2006.01)
*C07C 29/84* (2006.01)
*C12F 3/06* (2006.01)
*C12G 3/08* (2006.01)

(56) References Cited

U.S. PATENT DOCUMENTS

| | | |
|---|---|---|
| 5,480,665 A | 1/1996 | Smith |
| 6,019,034 A | 2/2000 | Ford, Sr. |
| 6,626,092 B2 | 9/2003 | Tarlow |
| 9,200,243 B2 | 12/2015 | Mosier |
| 10,428,298 B1 | 10/2019 | Salzman |
| 11,213,766 B1 * | 1/2022 | Rubin .................. B01D 3/001 |
| 11,772,009 B2 * | 10/2023 | Rubin .................. C07C 29/84 |
| | | 203/91 |
| 2013/0243922 A1 | 9/2013 | Lynn |
| 2014/0287110 A1 | 9/2014 | Mosier et al. |
| 2017/0260486 A1 | 9/2017 | Ottens et al. |
| 2020/0123481 A1 | 4/2020 | Davis |

OTHER PUBLICATIONS

You, Ling, et al. "Main flavor components separation pattern of luzhou-flavor Baijiu using vacuum distillation." (2020): 16-22, 7 pages.

Third Office Action received for Chinese Application No. 202180065204.1, dated Mar. 6, 2025, 19 pages.

Yang, Shengzhi, et al., "Application of Vacuum Solid-State Distillation in Xiaoqu Baijiu Production", Liquor-Making Science & Technology, No. 7, pp. 37-41, Jul. 18, 2020; 6 pages. English Abstract on p. 2.

* cited by examiner

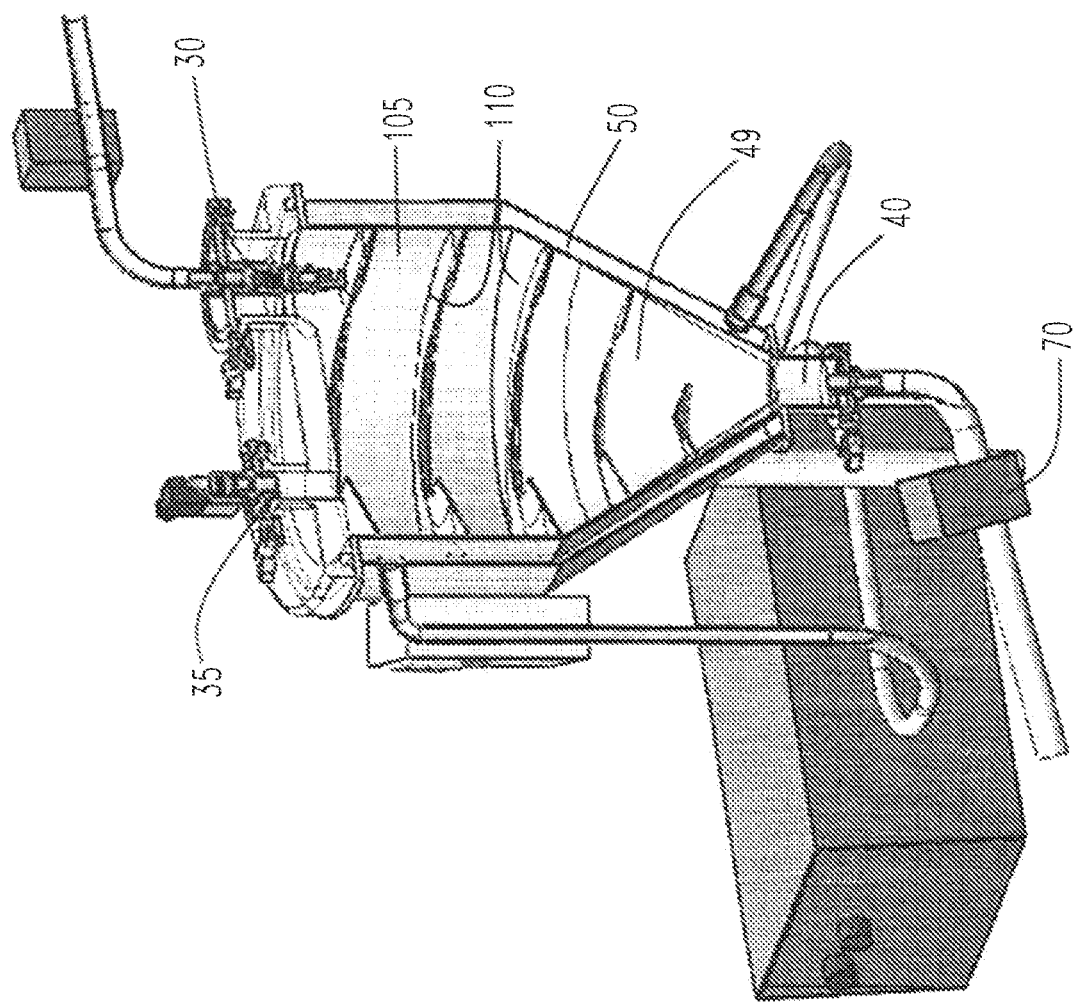

SYSTEMS AND METHODS FOR REHABILITATING ALCOHOL COMPOSITIONS AND REHABILITATED ALCOHOLIC PRODUCTS

CROSS-REFERENCE TO RELATED APPLICATIONS

This patent application claims priority to U.S. patent application Ser. No. 16/939,340, filed on Jul. 27, 2020, and also to U.S. Provisional Patent Applications Ser. Nos. 63/156,517, filed on Mar. 4, 2021; and 63/209,487 filed on Jun. 11, 2021.

TECHNICAL FIELD

The present disclosure relates generally to the field of alcoholic beverages, and more particularly, to systems and methods for removing adverse congeners from alcoholic compositions. Aspects of the disclosure also relate to alcoholic compositions with reduced quantities of congeners, including alcoholic compositions with improved organoleptic properties.

BACKGROUND

Alcoholic beverages have been a staple of humanity for thousands of years. Beer was instrumental in the building of the Egyptian pyramids as both inexpensive and enjoyable rations for the labor force, but also a means of converting non-potable water into a source of hydration. However, despite millennia of experience in fermenting and distilling alcoholic beverages, it remains difficult to consistently produce high-quality beer, wine, and liquor. Indeed, the quality of wine and liquor especially run the gamut from the very rare and fine to the barely drinkable.

The art of crafting of alcoholic beverages has remained a closely guarded trade for many years. Typically, aqueous solutions sweetened with a start of fruit sugar are fermented to produce ethyl alcohol as well as a variety of congeners (minor chemical constituents). While some of these congeners are desired as providing desirable organoleptic qualities, such as a certain richness of flavor, several others, such as methanol, acetaldehyde, butanol, isobutanol, methylbutanol, and the like, are known to cause hangover symptoms and/or impart a harsh flavor to the alcoholic beverage. While barrel aging alcohol is known to absorb some of the larger congener molecules and thus improve the taste of the alcohol, such a process is extraordinarily time consuming, often taking decades.

Beverage quality may vary greatly from manufacturer to manufacturer, as well as from batch to batch produced by a given manufacturer. This arises in part because of inconsistent processing and in part due to variations in the source and quality of raw materials. One source of variance in beverage quality is the presence of unwanted chemical species or congeners in the beverage generated as side effects of the fermentation/distilling processes and contributing adverse flavors to the beverage.

Many of these chemical species have boiling points very close to ethanol at standard pressure and are hard to remove by distillation without simultaneously removing substantive quantities of ethanol and/or other desirable congeners. Thus, there remains a need for means to quickly remove unwanted congeners from alcoholic beverages while leaving behind the ethanol and desired congeners/flavorings. The present disclosure addresses this need.

BRIEF DESCRIPTION OF THE DRAWINGS

FIG. 4E is a second cutaway view of the alcohol rehabilitation system of FIG. 4A having a raced interior wall.

DETAILED DESCRIPTION

Figure 1A:
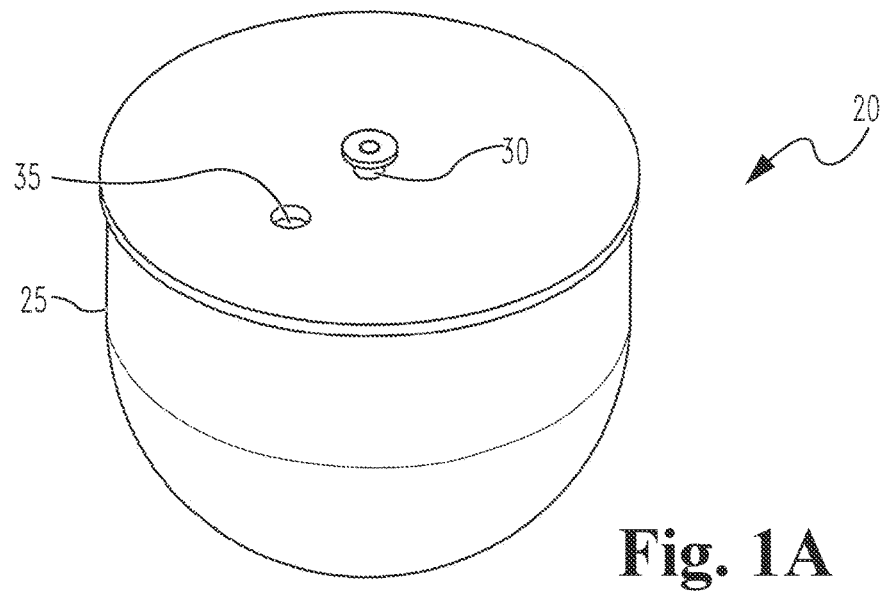
FIG. 1A is a perspective view of an alcohol rehabilitation system according to a first embodiment of the present disclosure.
Figures 1B, 1C:
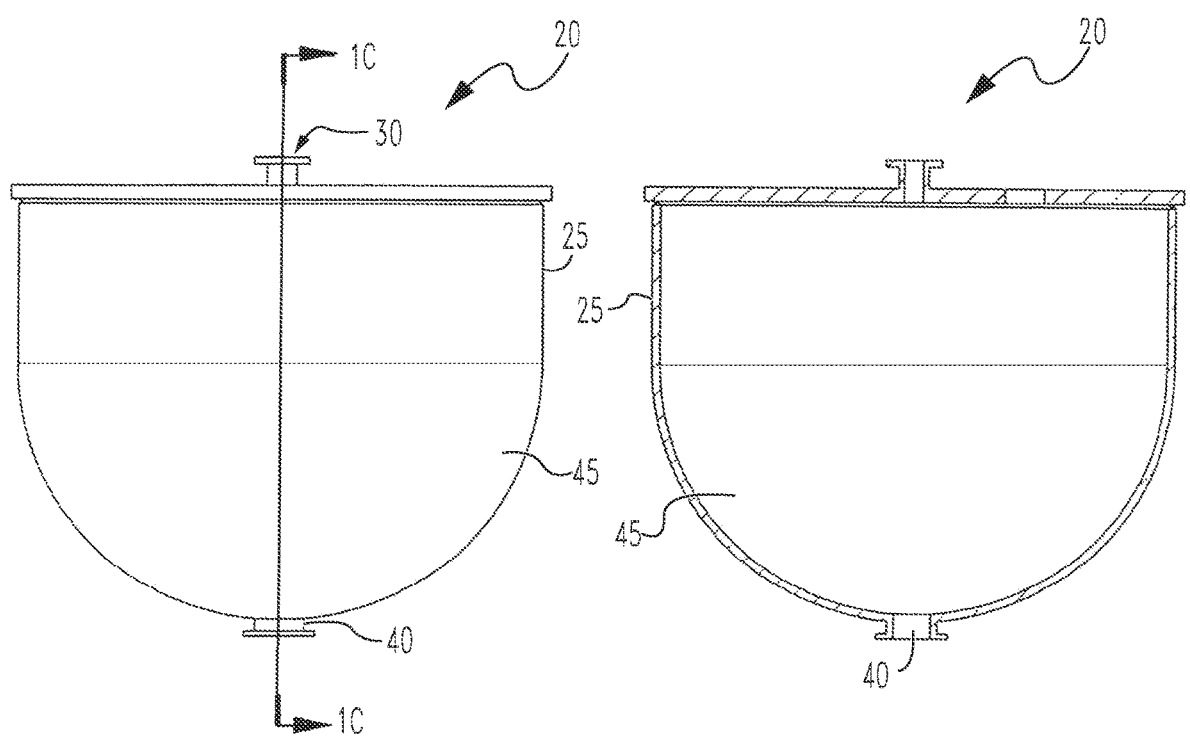
FIG. 1B is a side elevation view of the system of FIG. 1A.
FIG. 1C is a cutaway view of the system of FIG. 1B along line A-A'.
Figure 1D:
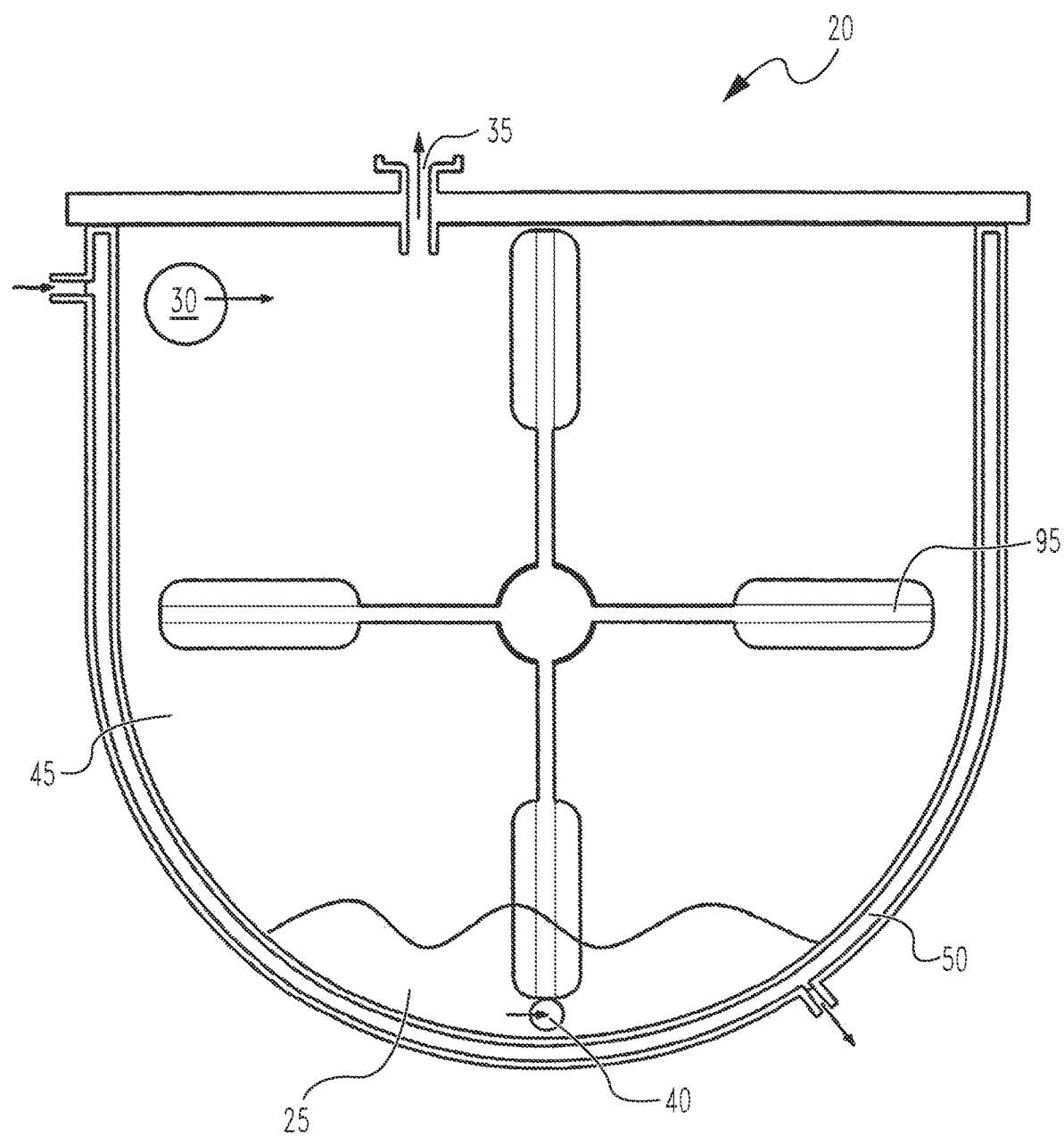
FIG. 1D is a cutaway view of the system of FIG. 1A showing internally mounted agitators.

For the purposes of promoting an understanding of the principles of the disclosure, reference will now be made to the methods, beverage compositions, and embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates.

Aspects of the disclosure relate to methods of removing unwanted congeners from an alcoholic composition and to alcoholic compositions (e.g., beverage compositions) comprising reduced levels of unwanted congeners. As used herein, "alcoholic composition" refers to a composition comprising ethanol. For the avoidance of doubt, it is to be understood that an alcoholic composition is substantially free of any alcohol(s) other than ethanol (e.g., methanol). For example, an alcoholic composition may comprise alcohol(s) other than ethanol in a total amount that is less than 1 percent by weight, less than 0.50 percent by weight, less than 0.25 percent by weight, less than 0.10 percent by weight, less than 0.05 percent by weight, less than 0.01 percent by weight, or less than 0.005 percent by weight. For example, an alcoholic composition may comprise alcohol(s) other than ethanol in a total amount that is less than 1 percent by volume, less than 0.50 percent by volume, less than 0.25 percent by volume, less than 0.10 percent by volume, less than 0.05 percent by volume, less than 0.01 percent by volume, or less than 0.005 percent by volume. As used herein, "alcoholic composition" may refer to beer, wine, liquor, or other ethanol-containing compositions fit for human consumption. As used herein, "removing" a congener from an alcoholic composition means reducing the quantity of that congener in the alcoholic composition. As used herein, where a congener is "removed" from an alcoholic composition, it is to be understood that the quantity of the congener may be reduced partly, substantially, or entirely or effectively entirely (i.e., to the point that it is not detectable by one or more analytical techniques) relative to the amount of congener present in the alcoholic composition before the congener was removed. In some embodiments, after a congener is "removed" from an alcoholic composition, the congener remains detectable in the alcoholic composition by one or more analytical techniques. In some embodiments, after a congener is "removed" from an alcoholic composition, the congener is not detectable in the alcoholic composition by one or more analytical techniques.

Removal of some or all of the unwanted congeners in an alcoholic composition may be desired because the unwanted congener(s) are inherently toxic or because the unwanted congener(s) (in their present concentration(s)) contribute an unpleasant or negative organoleptic experience. One congener found in alcoholic compositions is ethyl acetate (also referred to herein as "EA"). Ethyl acetate is an ester molecule formed through the esterification of ethanol (alcohol) and acetic acid (vinegar). Ethyl acetate is also a polar, aprotic solvent with amphipathic properties. As a result, consumers are highly sensitive to small changes in ethyl acetate concentration both in the olfactory reception, which may cause a rough peak and sharp bite in the finish, and in the cellular equilibrium which may cause a solvent-like burn on the rear of the oral cavity. Ethyl acetate has a very similar boiling point to that of ethanol. As a result, ethyl acetate is often concentrated rather than removed during distillation of spirits, which has led to the incorrect consumer correlation between bite and alcohol concentration or proof. In fact, it is the ethyl acetate concentration that controls the perceived "bite" characteristic in the peak and finish of fermented foods and beverages. Since ethyl acetate also serves as a polar-aprotic solvent during consumption, it may aid in the detection of other flavor molecules. As a result, an ethyl acetate concentration too low may inhibit a consumer's ability to detect other desirable flavors and aromas.

Proper balancing of ethyl acetate concentrations at the parts-per-million levels is necessary to optimize the organoleptic properties of foods and beverages. For example, ethyl acetate in very low quantities operates on certain combinations of specialized G protein-coupled olfactory receptors to yield a pleasant or enhanced organoleptic experience, while at greater concentrations ethyl acetate operates on those same receptors to generate an unpleasant or negative organoleptic experience. Such a negative organoleptic experience may be characterized by a bite, throat burn, bitterness, a metallic taste, a lingering aftertaste, head recoil, involuntary shudder, triggering of the gag reflex, and combinations thereof. Reduction or removal of ethyl acetate may eliminate these negative organoleptic experiences, and reduction of ethyl acetate concentration to certain levels may actually enhance the already desirable organoleptic properties of the alcohol.

In some embodiments, the methods disclosed herein are applied to produce a purified alcoholic composition, defined herein as an alcoholic composition from which a quantity of one or more unwanted congeners has been removed. For example, in some embodiments, the methods disclosed herein are applied to reduce the ethyl acetate concentration of an alcoholic composition to from 1 ppm (parts per million) to 400 ppm as measured in the liquid phase of the alcoholic composition as measured by gas chromatography mass spectrometry.

In some embodiments, the purified alcoholic composition is an organoleptically improved beverage comprising ethanol that has been prepared from a starting alcoholic composition. That is, in some embodiments, the methods disclosed herein are applied to produce an organoleptically improved beverage from a starting alcoholic composition, wherein the organoleptically improved beverage comprises ethanol. In some embodiments, the methods disclosed herein are applied to produce an organoleptically improved beverage from a starting alcoholic composition, wherein the organoleptically improved beverage comprises ethanol and wherein the starting alcohol-containing composition from which the beverage was derived possesses one or more undesirable organoleptic properties not found in the organoleptically improved beverage. In some embodiments, said one or more undesirable organoleptic properties are selected from the group consisting of harsh finish, sharp finish, biting finish, solvent finish, astringent finish, heavy finish, muted flavor, a solvent overtone in the peak and/or the finish, dry taste on the palate, a harsh peak that overshadows one or more flavors (e.g., one or more delicate flavors), bite, throat burn, bitterness, metallic taste, lingering aftertaste, cause of head motion, e.g., head recoil, head-shaking, head-tilting, or head-tensing, cause of involuntary physiological response, e.g., shudder, cause of gag reflex, and combinations thereof. In some embodiments, the methods disclosed herein are applied to produce an organoleptically improved beverage from a starting alcoholic composition, wherein the organoleptically improved beverage comprises ethanol. In some embodiments, the methods disclosed herein are applied to produce an organoleptically improved beverage from a starting alcoholic composition, wherein the organoleptically improved beverage comprises ethanol and wherein one or more desirable organoleptic properties of the beverage are at least substantially similar to at least one corresponding desirable organoleptic property of the alcohol-containing composition from which the beverage was derived. In some embodiments, the methods disclosed herein are applied to produce an organoleptically improved beverage from a starting alcoholic composition, wherein the organoleptically improved beverage comprises ethanol and wherein one or more desirable organoleptic properties of the beverage are substantially improved over the corresponding one or more corresponding desirable organoleptic properties of the alcoholic composition from which the beverage was derived. In some embodiments, said one or more desirable organoleptic properties are selected from the group consisting of smooth finish, rich finish, balanced finish, bright peak, flavorful peak, balanced peak, balanced peak that accentuates nuances of flavor, and combinations thereof.

Consumers often describe the transient experience of flavor in three unique phases including the 'start,' 'peak,' and 'finish,' which follow the corresponding sensory mechanisms of taste, smell, and a residual detection and molecular degradation. Each phase is dominated by specific sensory sources, and an over- or under-expression of flavor and aroma during each phase may determine the overall desirability of the food. Consumers initially begin with taste of the food or beverage on the tongue where they may experience a combination of tasting notes that may include sweet, sour, bitter, savory, fatty, and salty. Tasting notes are detected by multiple types and variants of receptors (commonly referred to as taste buds) primarily found on the tongue. While some tasting notes are governed by a single receptor type, other tasting notes, such as bitterness, may be perceived through a combined signal of more than twenty-five receptor variants. An over- or under-expression of any one of the receptors may cause alarm to the consumer and thereby decrease the food's perceived positive organoleptic properties. As a result, consumers often refer to organoleptically desirable foods or beverages as 'balanced.'

During consumption, taste may almost immediately be followed by smell, often described as the peak, as volatile aromas travel back down the throat and up into the olfactory cavity. The additional time needed for volatile compounds to travel from the oral cavity to the olfactory cavity creates the perceived time lag between the start and peak of a consumer experience. Smell is transmitted primarily through G-protein coupled olfactory receptors, with nearly one thousand different olfactory receptors responsible for smell, each which is highly sensitive to a particular molecule. Olfactory receptors are particularly selective to esters, such as ethyl acetate, a certain class of organic molecule that consumers often refer to as 'essences.' The senses of taste and smell differ in their sensitivities. For comparison, tastes may typically discern concentration changes in parts-per-hundred, while smell may discern changes in concentration of as little as parts-per-million. As with taste, the organoleptic properties of a food or beverage may be determined by the balance of smell experienced through a combination of receptors. An over- or under-expression of any one receptor may cause the perceived balance of a food or beverage to decrease, resulting in a less desirable product.

The finish in foods and beverages is more complicated than the start or the peak. During the finish molecules in the oral cavity begin to degrade through various mechanisms, such as hydrolysis and catalysis, volatile compounds promoted through the heat and convection in the oral cavity continue to evaporate from the oral cavity and travel to the olfactory cavity, and the cellular equilibrium of the oral cavity itself begins to alter as a result of the food or beverage. Foods or beverages that drastically alter the oral cavity during consumption often have a finish described as 'sharp,' 'hot,' or 'biting' (examples include hot sauce, shelf-stable condiments, or spirits). In low concentrations, these undesirable experiences may be described as 'rough,' 'heavy,' astringent, full of tannins, or the like. On the other hand, foods and beverages that maintain the taste, smell, and cellular equilibrium as they dilute on the palate are often referred to as having a 'fresh,' 'savory,' 'crisp,' 'smooth,' 'delicate,' or 'refined' finish, and are typically considered more desirable.

The vapor pressure and perceived concentration of ethyl acetate does not directly correspond to the molecular concentration due to the complex intermolecular interactions in a given food or beverage. Thus, balance may not simply be controlled through measurement and titration. A properly balanced food or beverage may instead create a condition in which an ethyl acetate equilibrium (also referred to herein as an "EAE") may be perturbed and re-established under a different concentration. The present technology achieves this goal (perturbing an ethyl acetate equilibrium of an alcoholic composition and re-establishing it under a different concentration) without altering the concentration of other desirable molecules (e.g., ethanol) through the use of food or beverages' complex steric hindrance. In this way, the bite or roughness typically experienced by consumers from ethyl acetate and other fermentation byproducts present in an initial alcohol composition may, through methods disclosed herein, be rebalanced to a more organoleptically favorable condition in a resulting organoleptically improved beverage. Through this process, smells in the peak of a consumer experience will often be perceived as brighter and more defined since they are not competing with ethyl acetate, and the finish will often be perceived as 'smoother' and more 'refined,' thereby creating more desirable organoleptic properties in the resulting organoleptically improved beverage.

Along these lines, a further aspect of the disclosure relates to methods of measuring vapor phase ethyl acetate concentration in alcoholic compositions and the use of said methods to optimize the organoleptic properties of alcoholic compositions. Conventional methods of measuring congener concentration (e.g., ethyl acetate concentration) in alcoholic compositions such as wine, beer, spirits, as well as fermentation byproducts, such as natural or distilled vinegar utilize direct infrared, HPLC, and/or gas chromatography mass spectrometry measurement of the liquid phase of the sample. Conventional wisdom is if the chemical makeup is the same, or at least very similar, then the flavor should be the same, or at least very similar. While these methods are very good at measuring absolute congener concentrations in a beverage, they have been found to correlate to flavor only loosely and have not been found to be consistent enough to predict the organoleptic properties of alcoholic compositions. Without wishing to be bound by theory, it is believed that one reason for the lack of correlation and/or consistency is that the consumer experience of flavor is the result of complex intermolecular interactions with multiple sensor phases. While taste sensors on the tongue are important in determining the basic flavor of a beverage, most of the nuances of flavor and aromatic complexities are experienced through the olfactory. The utilization of these precise instruments to fingerprint the consumer flavor experience has often been found to be inaccurate.

Aspects of the present disclosure address those issues. In some embodiments, the olfactory experience of a beverage may correctly be correlated by measuring the partial pressure of volatile molecular components sampled from the atmosphere in fluidic communication with a liquid phase and/or solid phase sample of the beverage that has reached equilibrium saturation under closed system conditions. The atmospheric phase equilibrium may be established with air and/or inert gas phase environments under ambient pressures and temperatures. In some embodiments, the temperature of the sample and/or the atmosphere may be adjusted to match the preferred consumption conditions of the beverage. In the present method, complex intermolecular interactions in the liquid and/or solid phase of the sample beverage may be controlled for by establishing a quasi-equilibrium condition with a vapor phase. While the liquid phase concentration of molecular constituents, such as ethyl acetate, may shift from beverage to beverage, the atmospheric phase concentration may remain relatively consistent and therefore represent a more accurate representation of the olfactory experience and, therefore, of the organoleptic properties of a beverage.

In an embodiment of the disclosed method, a 1 mL to 5 mL sample is placed in a vial having a total volume of 0.5 to 5 times the sample volume, which is then sealed with a separate cap to form an isolated atmosphere. The sealed sample may be allowed to rest undisturbed, or may alternatively be agitated, such as for a period of from 5 seconds to 5 minutes or until an equilibrium condition is established between the atmospheric phase and the sample. A portion of known volume of the vapor phase is be removed from the vessel, analyzed using gas chromatography mass spectrometry, and examined for specific concentrations of molecules in the vapor phase. Alternatively, or in addition, the portion of known volume of the vapor phase is analyzed using one or more chemically selective sensors that are placed in fluidic communication with a sample of the equilibrium atmosphere. For real-time analysis, a chemically selective sensor may be placed in direct atmospheric communication with the isolated environment and partial pressure concentrations of select molecules may be detected through correlative and calibrated signals. In some embodiments, the chemically selective sensor may be specific for detection and measurement of ethyl acetate. When such an ethyl acetate-specific sensor is employed, a real time analysis of the organoleptic properties, particularly the smoothness of an alcoholic beverage, may be predicted by measuring the ethyl acetate partial pressure of a gas phase equilibrium above the sample beverage.

A further aspect of the disclosure relates to apparatuses and their use in reducing the quantity of one or more unwanted congeners in an alcoholic composition. For example, as shown in FIGS. 1A-8, an aspect of the present disclosure relates to an apparatus 20 for preferentially removing quantities of one or more predetermined unwanted congeners (typically fermentation biproducts), such as ethyl acetate, from alcoholic compositions such as beer, wine, liquor, and like beverages. In one embodiment, the apparatus 20 includes a pressure vessel 25 having a liquid inlet port 30, a vapor outlet port 35, and a liquid outlet port 40, all in fluidic communication with an internal pressure controllable chamber 45 defined by the pressure vessel 20. The pressure vessel 25 typically includes a water jacket 50 or like temperature controller at least partially enveloping the pressure chamber 45 and in thermal communication with the same. Liquid inlet port 30 is typically connected in fluidic communication, such as via a pipe 55, with a liquid pump 60. Pump 60 is connected in fluidic communication with alcohol source 65. Typically, at least one valve 70 is operationally connected in line between alcohol source 65 and liquid inlet port 30. The valve 70 may be connected between inlet port 30 and pump 60, between pump 60 and alcohol source 65, or valves 70 may be connected in both positions.

Vapor outlet port 35 is typically connected in fluidic communication with a vacuum pump 75, which is connected in fluidic communication with a collection vessel 80. Vacuum pump 75 typically operates to remove and direct evolved vapor from the pressure vessel 25 for collection in the collection vessel 80 at a desired pressure, as well as establish a partial vacuum within the pressure controllable chamber 45. The collection vessel 80 may be a cold trap, a pressure-controlled vessel, or the like. Typically, at least one valve 70 is operationally connected in line between collection vessel 80 and vapor outlet port 35. The valve 70 may be connected between vessel 45 and pump 75, between pump 75 and outlet port 35, or valves 70 may be connected in both positions. Collection vessel 80 may be emptied and the accrued distillate recovered.

Liquid outlet port 40 is typically connected in fluidic communication with pump 85, which is connected in fluidic communication with alcohol collection vessel 90. Typically, at least one valve 70 is operationally connected in line between alcohol collection vessel 90 and liquid outlet port 40. The valve 70 may be connected between vessel 45 and pump 85, between pump 85 and collection vessel 90, or valves 70 may be connected in both positions. Typical vessel 45 throughput is about 0.025 liters per minute to 1.0 liters per minute per liter of chamber volume, more typically between 0.1 liters per minute and 0.8 liters per minute per liter of chamber volume, and more typically between 0.25 liters per minute and 0.6 liters per minute per liter of chamber volume.

Example 1

As illustrated generally in FIGS. 1A-1E, the above-described assembly 20 may be embodied to treat alcoholic compositions on a batch-by-batch basis. Pressure vessel 25 includes ports 30, 35, 40 as described above, as well as water jacket 50 or like temperature control mechanism encapsulating pressure chamber 45 in thermal communication therewith. Agitator 95 is positioned within pressure chamber 45 to facilitate stirring/vibration/bubbling of a volume of alcoholic beverage contained therein. A partial vacuum in pressure chamber 45 may be established via energization of vacuum pump 75.

Figure 1E:
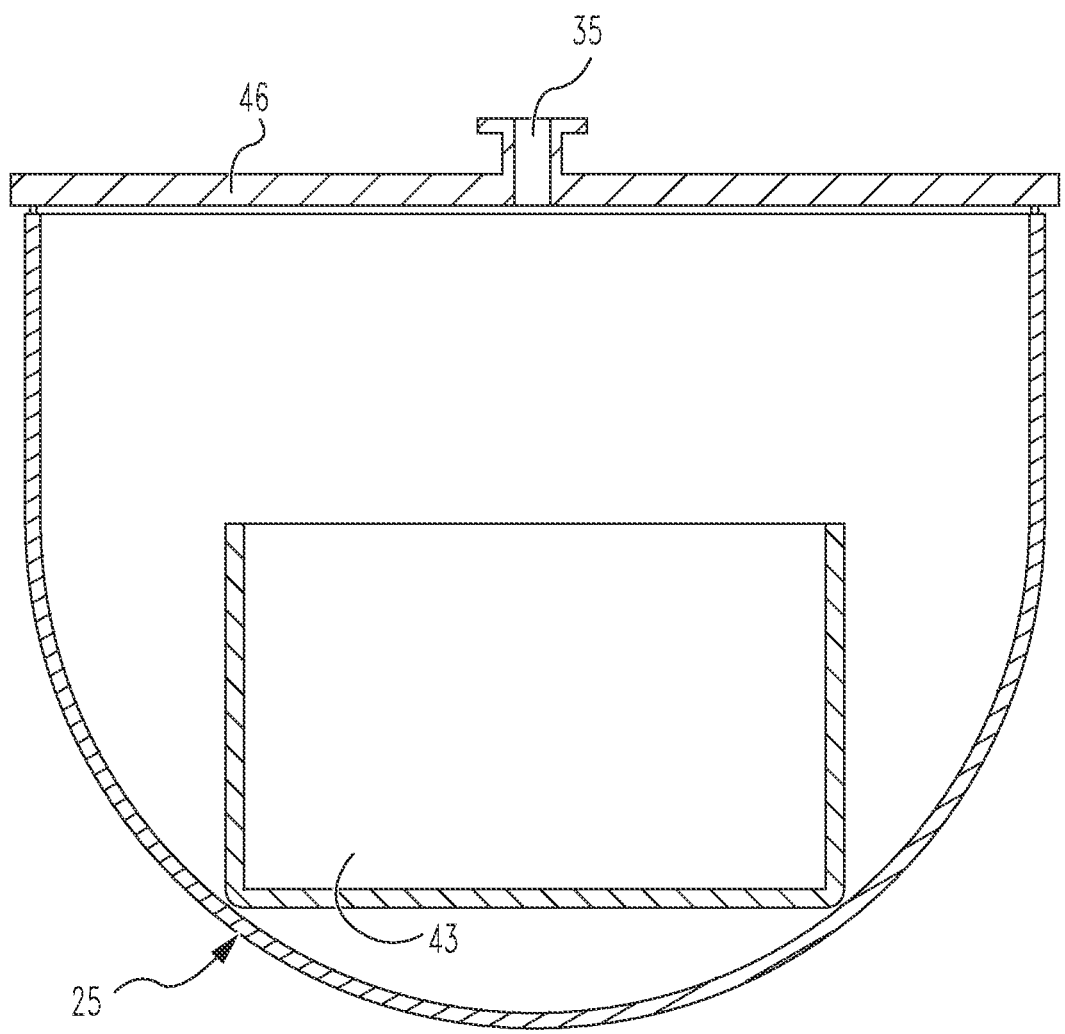
FIG. 1E is a cutaway section view of the alcohol rehabilitation system of FIG. 1A with a secondary open container positioned therein.

In FIG. 1E, an alcoholic composition contained in an open container 43 is placed in the pressure chamber 45. A vacuum lid 46 is then engaged with the vacuum chamber 45, thereby isolating the vacuum chamber environment from the surrounding exterior environment, and the pressure in the vacuum chamber 45 is decreased by energization of a vacuum pump 75 in operational communication with the vapor outlet port 35. Once the vacuum chamber pressure reaches a specified level, the vacuum chamber pressure is then increased to atmospheric pressure and the lid 46 is removed, followed by the container 46 containing the now vacuum-treated alcoholic composition.

Example 2

Figure 2:
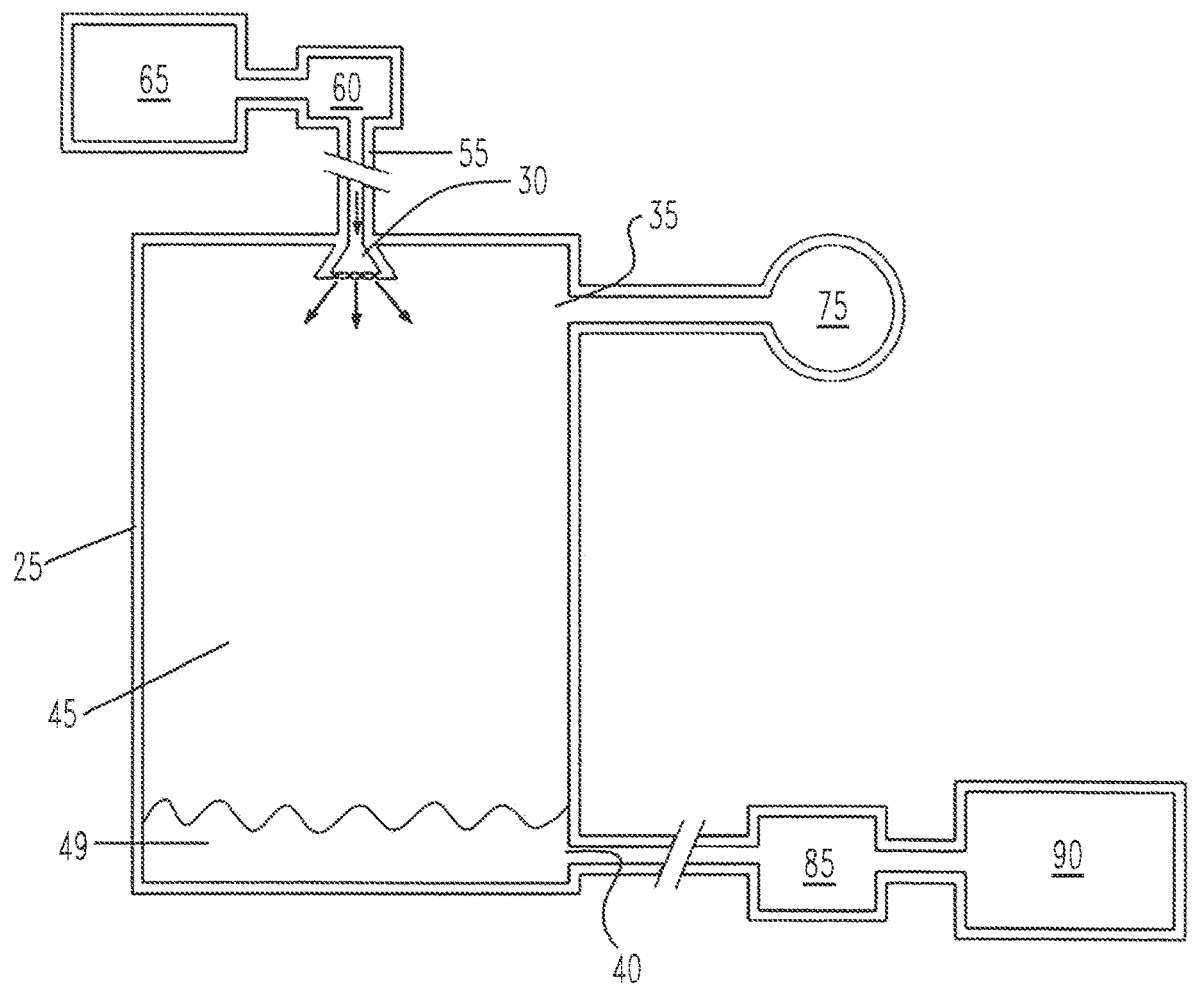
FIG. 2 is a cutaway section view of an alcohol rehabilitation system according to a second embodiment of the present disclosure.

As illustrated in FIG. 2, the above-described assembly 20 may take an embodiment to treat alcoholic compositions as a continuous flow process. Liquid inlet port 30 is configured as a spray head and is positioned to spray alcoholic composition pumped from source tank 65 into the pressure chamber 45 already pumped down to the desired partial vacuum pressure. The spray of alcoholic composition travels through the pressure chamber 45 to collect or pool at the bottom of the pressure vessel 25, where it may be pumped out through outlet port 40. In some embodiments, inlet port 30 is configured as a nozzle, while in other embodiments a separate nozzle is operationally connected to inlet port 30 to accelerate and direct the incoming liquid.

Example 3

Figure 3:
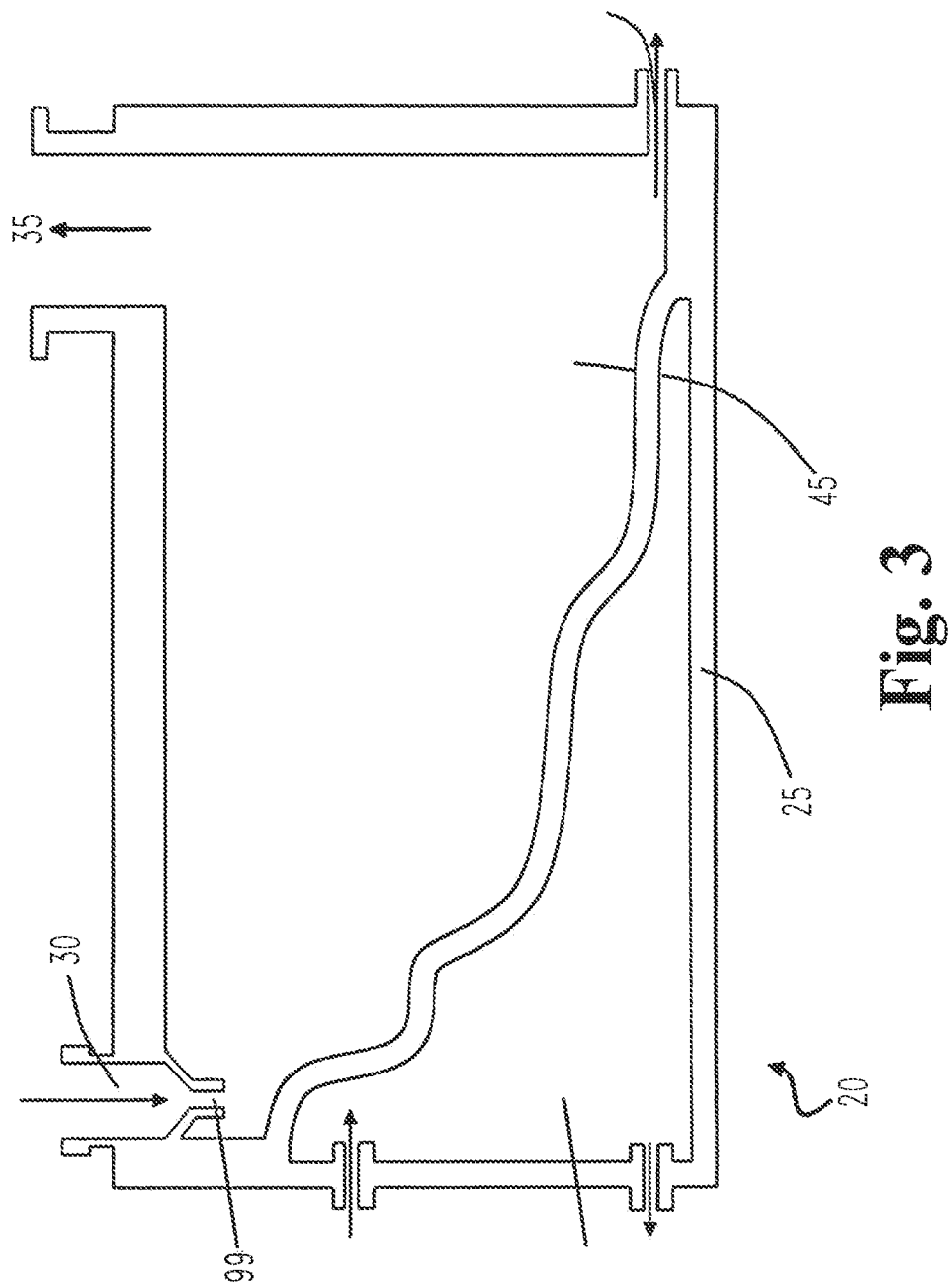
FIG. 3 is a cutaway section view of an alcohol rehabilitation system according to a third embodiment of the present disclosure.
Figure 4A:
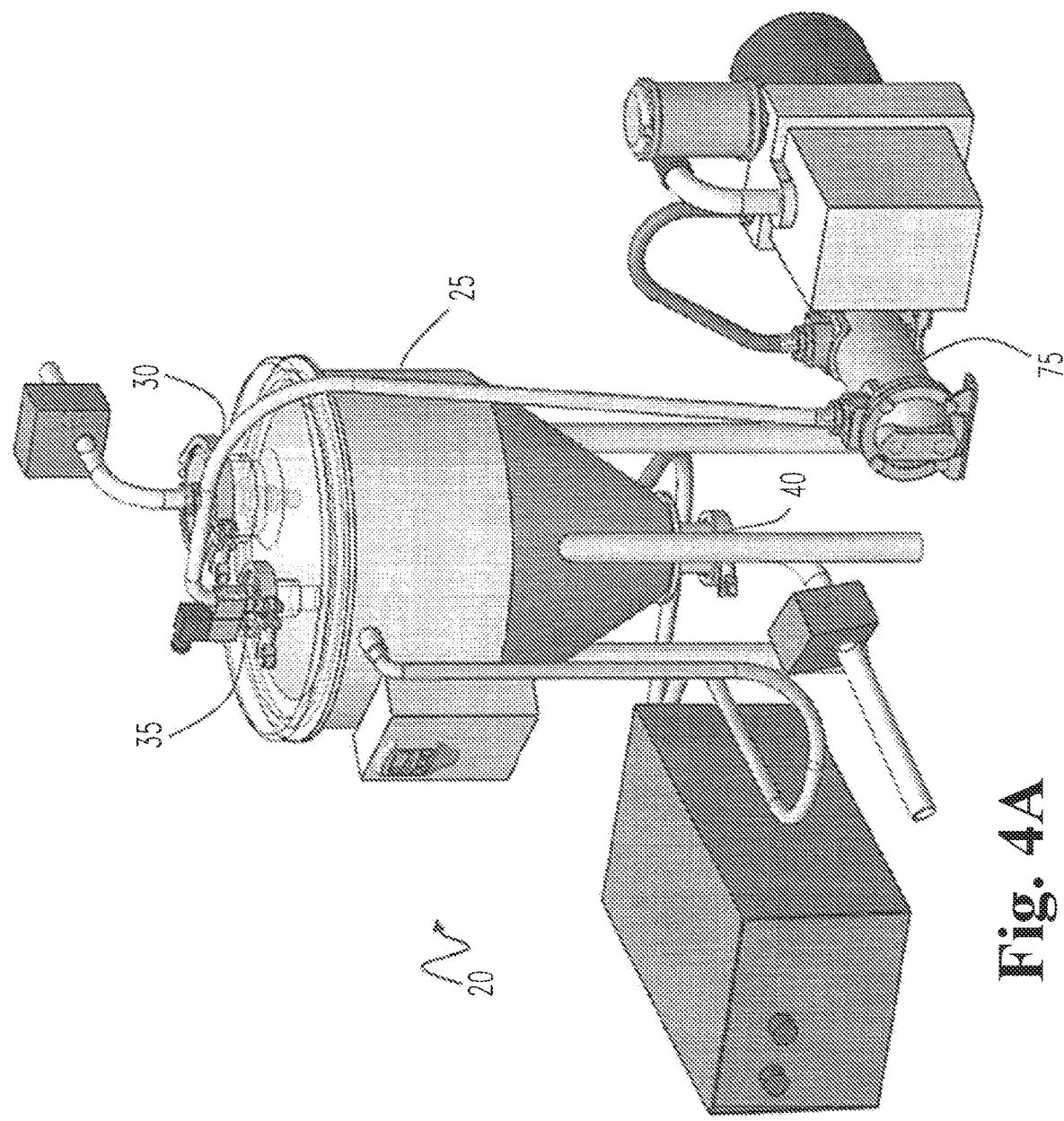
FIG. 4A is first perspective view of an alcohol rehabilitation system according to fourth embodiment of the present disclosure.
Figure 4B:
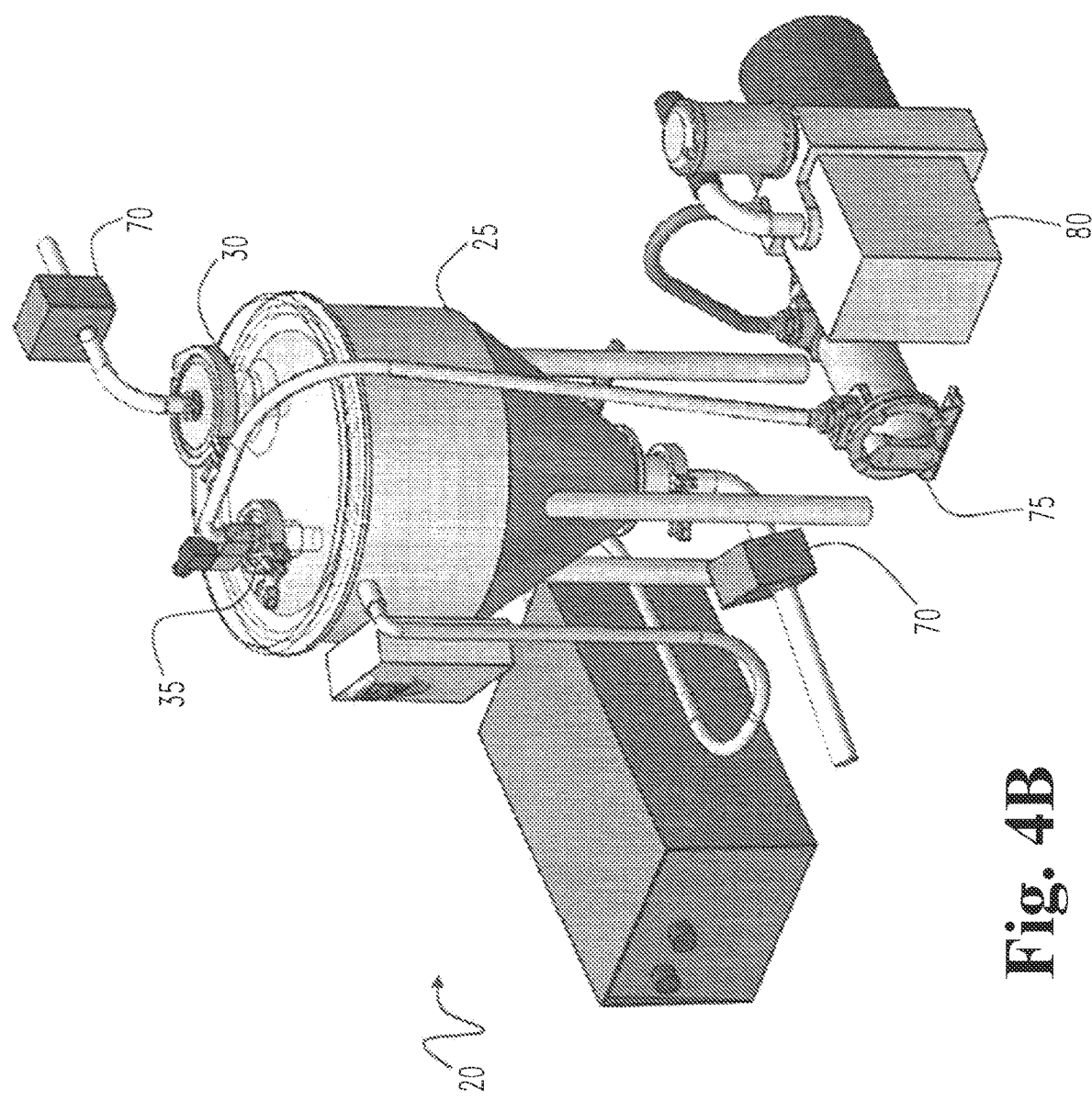
FIG. 4B is a second perspective view of the alcohol rehabilitation system of FIG. 4A.
Figure 4C:
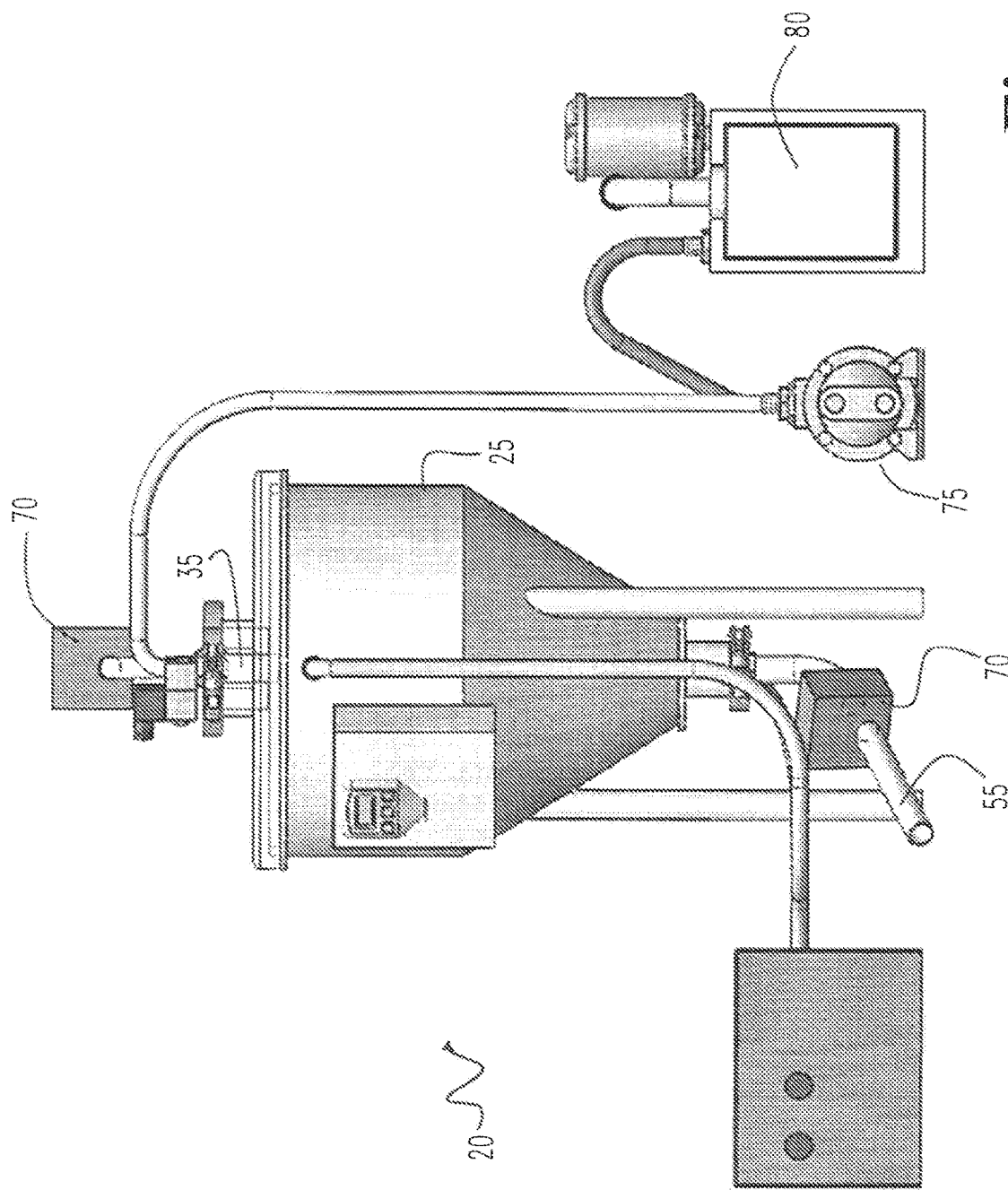
FIG. 4C is a front view of the alcohol rehabilitation system of FIG. 4A.
Figure 4D:
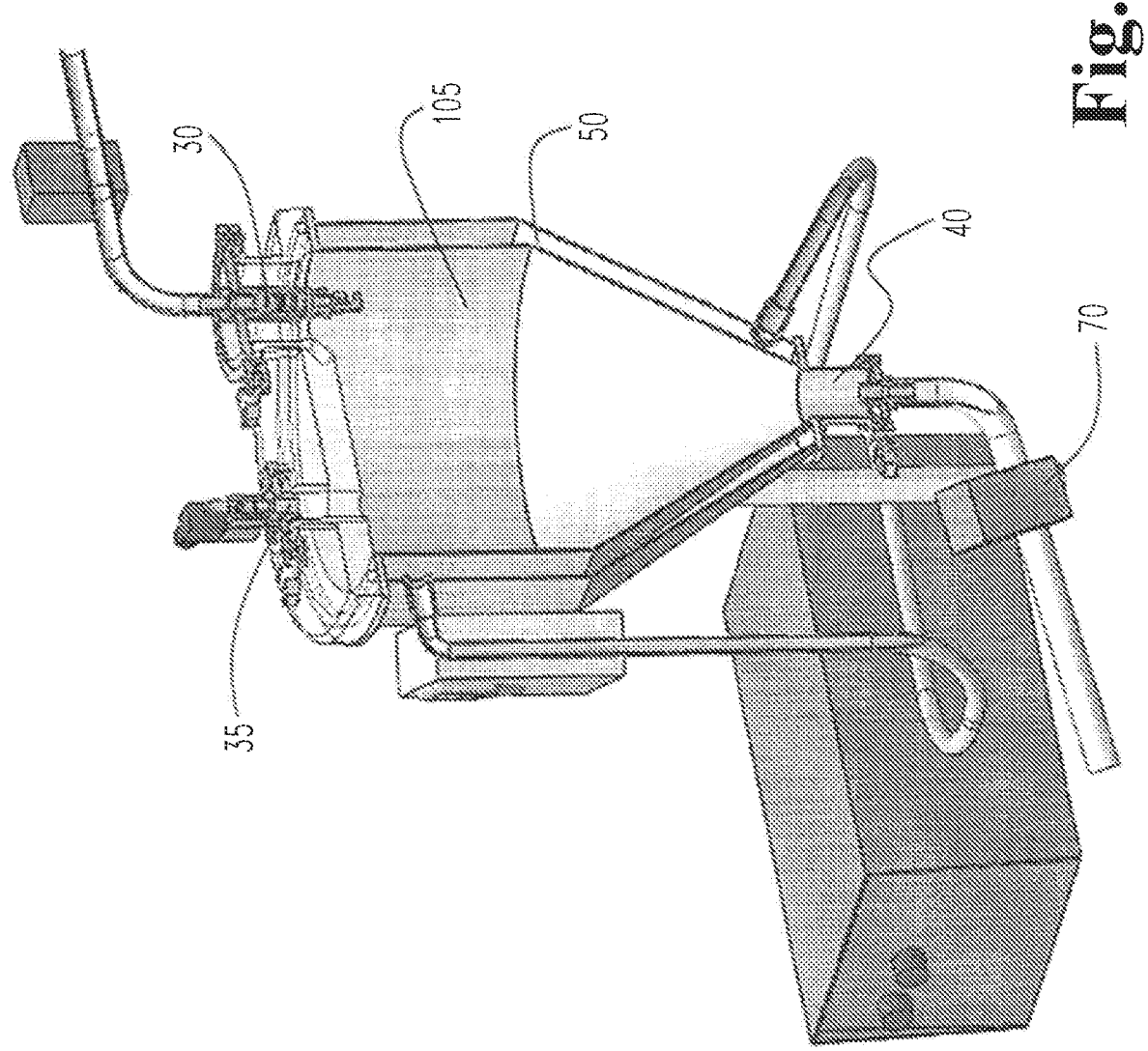
FIG. 4D is a first cutaway view of the alcohol rehabilitation system of FIG. 4A having a smooth interior wall.
Figure 4F:
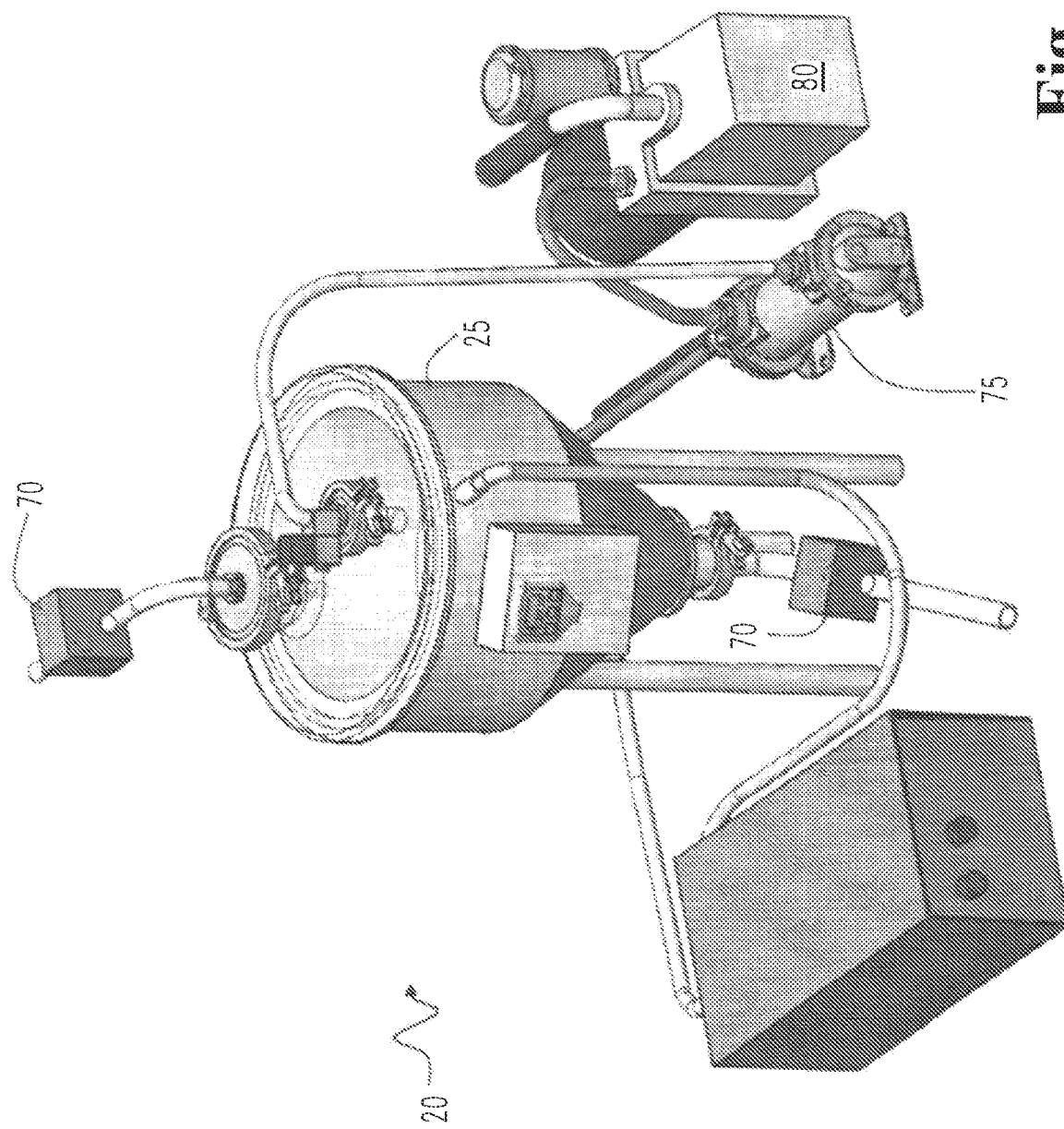
FIG. 4F is a third perspective view of the alcohol rehabilitation system of FIG. 4A.

As illustrated in FIG. 3, the above-described assembly 20 may take another embodiment to treat alcoholic compositions as a continuous flow process. The liquid inlet port 30 may empty onto one end of a ramp 100 where alcoholic composition pumped from source tank 65 spreads into a thin layer or sheet and flows downhill to pool at the other end of the ramp 100. Congeners may be evolved from the flowing ethanol sheet into the partial vacuum environment inside the pressure chamber 45 when the vacuum pump 75 is energized. The treated alcoholic composition may be pumped out of pressure chamber 45 and into collection vessel 90.

Example 4

As illustrated in FIGS. 4A-4E, the above-described assembly 20 may take still another embodiment to treat alcoholic compositions as a continuous flow process. Vessel 25 is typically acorn-shaped, with a circular top to bottom cross-section that decreases in diameter from top to bottom (in this example, the top-down sectional profile has a cylindrical portion atop a conical portion), and a chevron-shaped side sectional profile (in this example, the side sectional profile has a rectangular upper portion and a triangular lower portion). Vessel typically includes a water jacket exterior 50 encasing a pressure controllable chamber interior 45. Liquid inlet port 30 positioned near the top of the vessel 25 injects alcoholic composition pumped from tank 65 into pressure chamber 45 wherein injected alcoholic composition is under sufficient pressure upon injection to be moving quickly enough to follow a spiral path along the inside of the pressure chamber 45 and ultimately pool at the bottom. Typically, the alcoholic composition defines a thin stream or ribbon that circles the vessel 25 a plurality of times while the partial vacuum therein (as provided by the energized vacuum pump 75 connected in fluidic communication therewith) evolves unwanted congeners therefrom to yield a purified alcoholic composition as defined above. The purified alcoholic composition pools at the bottom of the pressure chamber 45 and may be pumped therefrom via liquid pump 85 into collection vessel 90. In some embodiments, the inside wall 105 of pressure chamber 45 is grooved or contoured 110 to help guide flowing alcoholic composition in a helical path from inlet port 30 to outlet port 40. Typically, the inside wall 105 would include a helical groove or race 110 to guide inlet liquid from the inlet port 30 around the inner wall several times to the outlet port 40.

In other like embodiments, vessel 25 may have convex or concave (see FIG. 5A) interior sectional contours. A concave shape profile may enable slow post inlet port liquid flow, followed by a deep cavity or reservoir formed near the outlet port 40 for sump modulation.

Ports 30, 35, and 40 of a first pressure chamber 45 may be in connected fluidic communication with other ports 30, 35, and 40 of other similar or identical pressure chambers 45 such that a plurality of pressure chambers 45 may be run in parallel from central vacuum 75 and fluidic pumps 60, 85. In this embodiment, fluid may be regulated individually or at fluidic manifolds connected in liquid communication with each respective pressure chamber 45.

In some embodiments, a floater valve 91 may be used to prevent dry sump of the liquid outlet port 30 and regulate a minimum sump level. Under operation a floating valve 91 may open the liquid outlet port 40 once sufficient liquid enters the chamber 45. In the case where the liquid outlet pump 85 removes liquid sufficiently fast to decrease the liquid below float level, the floater valve 91 may form a pressure gradient between the vessel 45 and liquid outlet pump 85 preventing further liquid removal. One added benefit of a floater valve 91 is to prevent vessel atmosphere from being pressurized back into the cleaned or treated liquid leaving the liquid outlet port 40.

Sensors 93 may also be used to provide feedback to regulator valves 94 to maintain a positive volume above liquid outlet port 40 and prevent depressurization of vessel atmosphere in the process fluid. Sensors 93 may be in direct communication with the vessel sump liquid (typically vacuum-treated alcoholic composition), such as in the case of optical, inductive, or acoustic sensors 93, or indirectly monitor the fluid level with an acoustic, ultrasonic, or thermal sensors 93 around the fluid outlet port 40.

Liquid pumps 60, 85 as described herein may be variable displacement pumps, in the case of diaphragm pumps or piston pumps, or may be fixed displacement pumps, in the case of turbine pumps. Fluidic pumps 75, 85 in communication with the outlet ports 35, 40 may experience thirteen to fifteen PSI of negative pressure and may need to be combined in series to provide sufficient suction; as used herein, 'vacuum pump' may mean a single pump unit or a plurality of pump unites operationally connected in series. An intermediate re-pressurization chamber 98 may also be used between multiple fluidic pumps 60, 85.

Vacuum pumps 75 of the present disclosure may be variable displacement pumps, such as piston pumps, rotary screw pumps, or rotary vane pump, or fixed displacement pumps, in the case of multi-stage regenerative blowers. Cold traps of the present disclosure may also result in pressure gradients and function as vacuum pumps. Cold traps may be electrically cycled, or may be fed using cryogenic media, such as dry ice or liquid nitrogen.

Fluid flow may be regulated by modulating valve cross-sectional area, or by repeatedly opening and closing the valve. Automated valves may be energized, such as pneumatically or electrically, and controlled by a PLC in operational communication with a digital pressure meter.

A fluid inlet nozzle may be connected in fluidic communication with inlet port 30 to direct the flow of the liquid into the vessel 45. The liquid may flow directly along the gravitational path or may flow in a helical manner as it proceeds down an interior vessel wall. Helical paths may be used to increase retention time and disrupt the surface tension of the fluid, and may benefit from a nozzle 99 with a narrowing throat to increase velocity prior to injection resulting in increased retention times for longer exposure to vacuum conditions. The terminal end of a fluid inlet nozzle 30 may be located sufficiently close to a vessel wall 105 to prevent droplet formation and splashing, with typical distances less than fifteen centimeters and typically less than two centimeters from the vessel wall 105. Laminar flow inlets may be used to decrease splashing and volatilization occurring during injection. Alternatively, a single or a plurality of liquid inlet openings 30 may enable a quasi-uniform flow of liquid to sheet along the inner wall of the vessel 45 to the liquid outlet port 40.

Figure 5A:
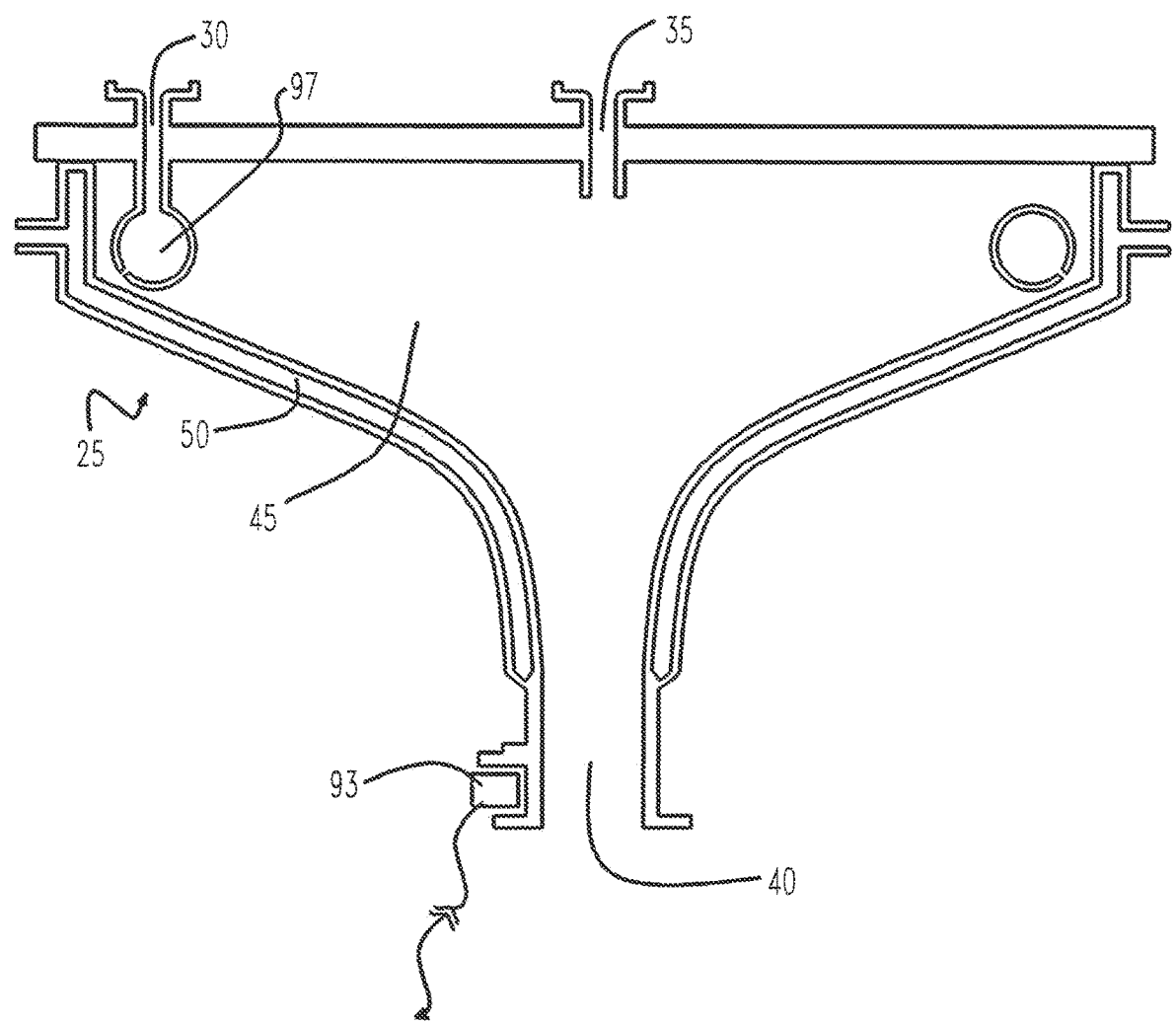
FIG. 5A is a cutaway view of pressure vessel of the embodiment of FIG. 4A wherein the vessel has concave interior sidewalls and features a fluid inlet body (manifold).
Figure 5B:
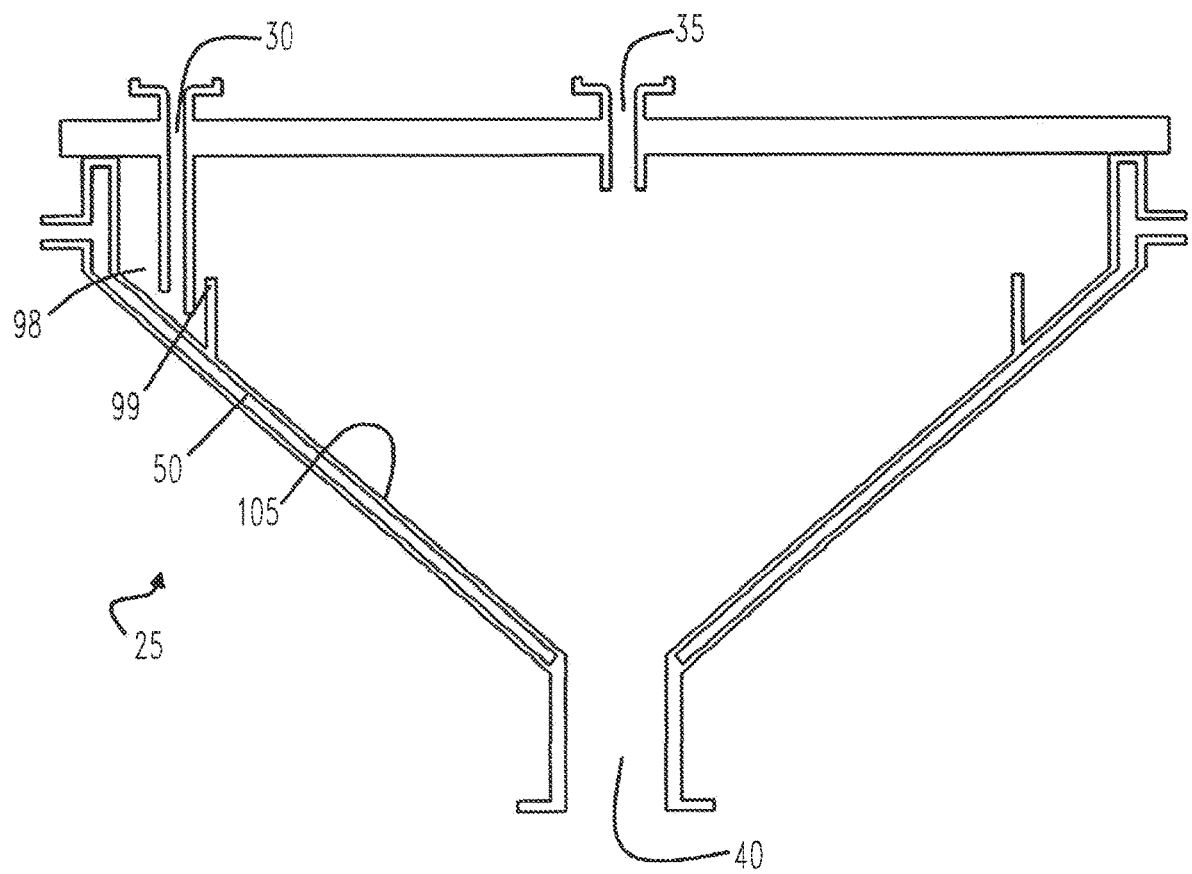
FIG. 5B is a cutaway view of pressure vessel of the embodiment of FIG. 4A wherein the vessel has an inlet trough operationally connected to the inlet port.
Figures 6A, 6B:
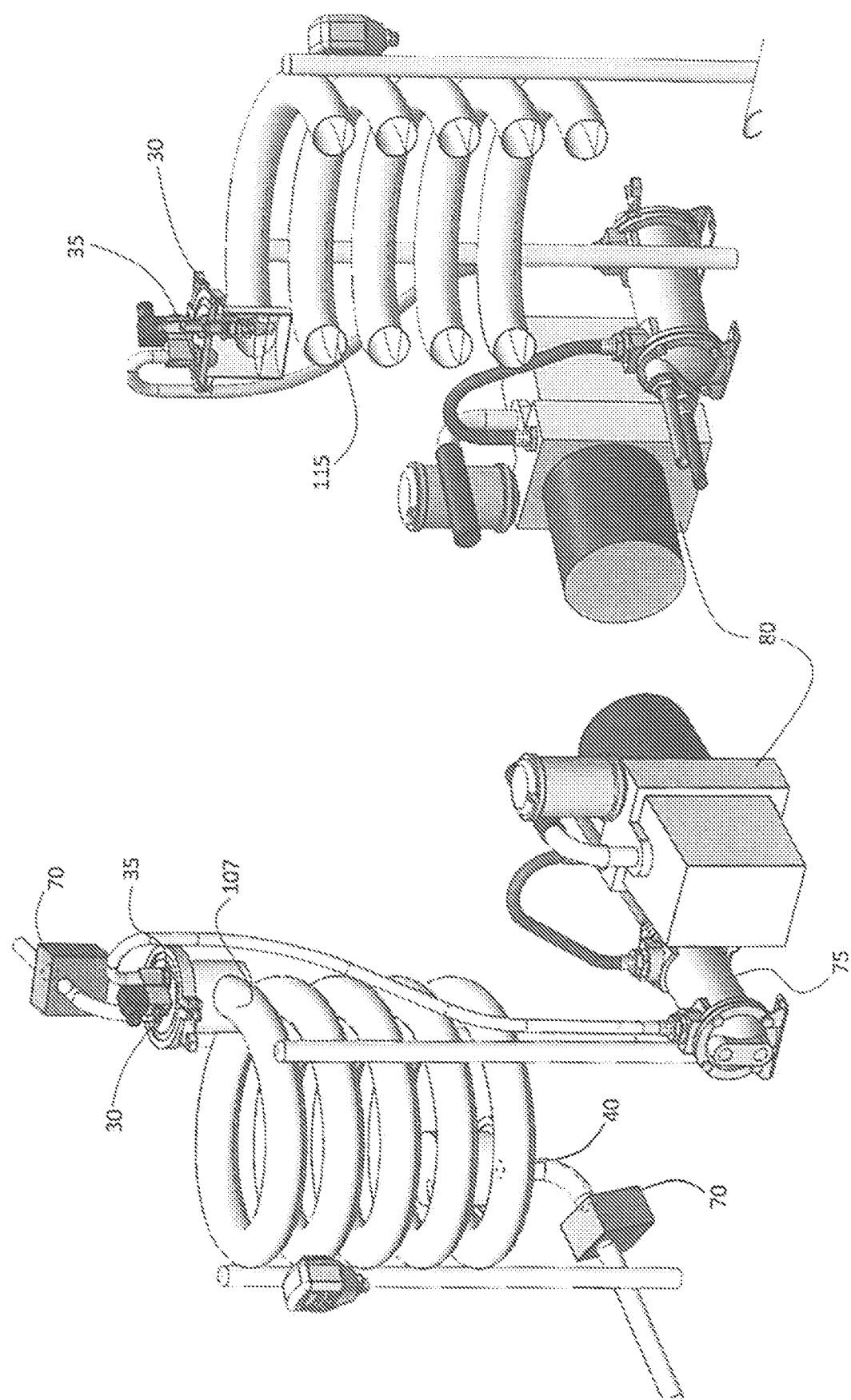
FIG. 6A is perspective view perspective view of an alcohol rehabilitation system according to fifth embodiment of the present disclosure.
FIG. 6B is a cutaway view of the embodiment of FIG. 6A.
Figure 7:
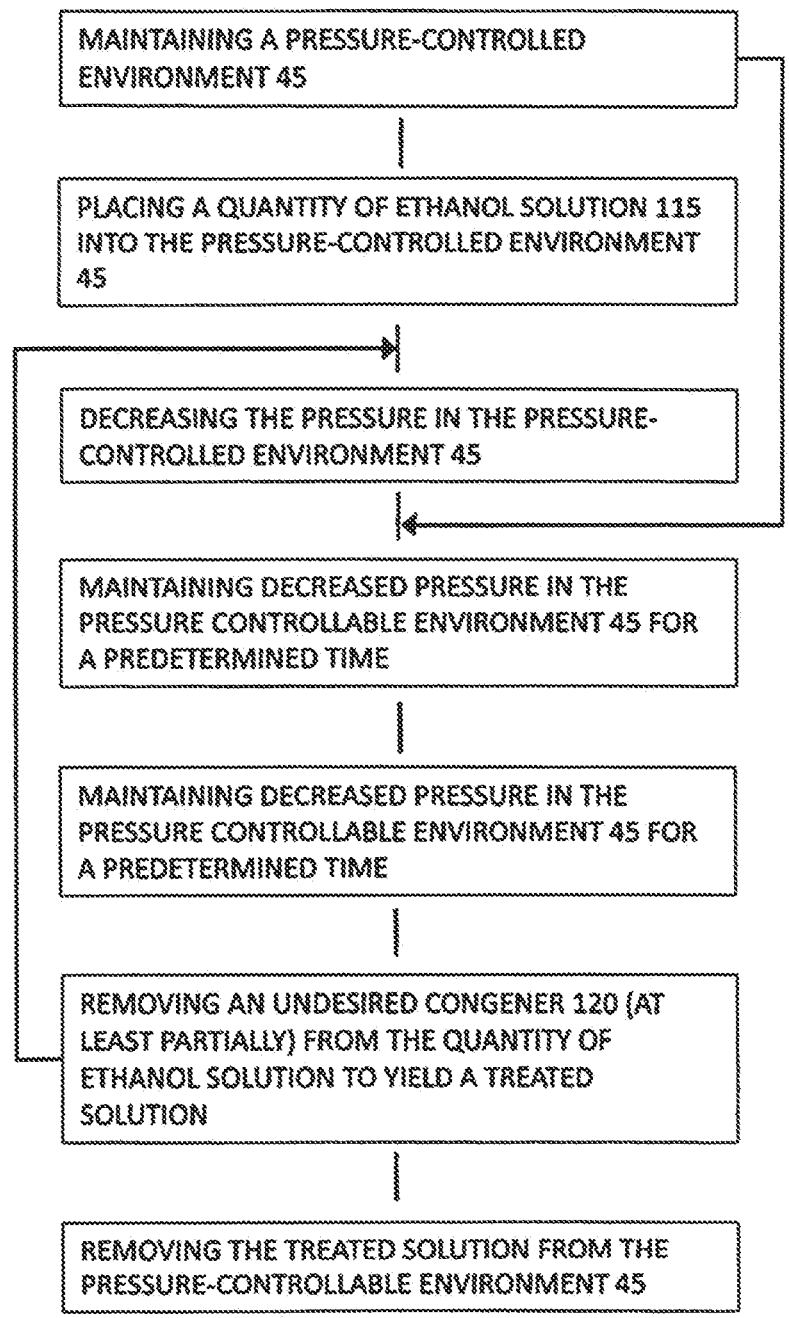
FIG. 7 is a schematic view of a method for rehabilitating alcohol underlying the operation of the above embodiments.

A liquid inlet body 97 may be used to decrease the pressure drop between a pressure regulator and vacuum vessel 45 by enabling liquid accumulation prior to injection (see FIG. 5A). In this case, liquid enters a manifold 97 a volume of space, such as a large tube, at least partially encircling the upper lip of the vessel 45. The cross-sectional area of the inlet body 97 is large relative to the inlet valve 31 enabling fluid to partially decrease in pressure prior to entering the vessel 45, which enables lower head pressures and slower flow. In another embodiment the liquid inlet body 97 may comprise bilateral pieces that may or may not be incorporated into the lid of the vessel. Bilateral separation may be used to enable rapid disassembly.

In one embodiment, the inlet body 97 is maintained above fifty-five Torr, while the vessel 45 is maintained below fifty-five Torr. In this case pressure may be substantially decreased without significantly altering the liquid composition prior to entering the bulk vessel volume. Inlet body 97 may be maintained at pressures such as 760 Torr, 700 Torr, 500 Torr, 400 Torr, 200 Torr, 100 Torr, 75 Torr, or the like. The vessel 45 may be maintained at pressures such as 50 Torr, 46 Torr, 45 Torr, 42 Torr, 40 Torr, or the like. In some embodiments, the vessel is maintained at a pressure from 40 Torr to 80 Torr, such as from 40 Torr to 60 Torr, from 40 Torr to 50 Torr, from 45 Torr to 65 Torr, from 50 Torr to 70 Torr, from 50 Torr to 65 Torr, or from 50 Torr to 60 Torr. In some embodiments, the vessel is maintained at a pressure that is selected based on the percent alcohol by volume (ABV) of the starting alcohol composition. For example, the vessel may be maintained at a pressure of 50 Torr for a 50% ABV alcohol composition, at a pressure of from 40 Torr to 50 Torr for a 40% ABV alcohol composition, at a pressure of from 55 Torr to 65 Torr for a 30% ABV alcohol composition, at a pressure of from 55 Torr to 65 Torr for a 20% ABV alcohol composition, at a pressure of from 50 Torr to 60 Torr for a 10% to 20% ABV alcohol composition, or at a pressure of from 65 Torr to 75 Torr for a 1% to 10% ABV alcohol composition.

A separate pressure drop vessel may be used to gradually step the pressure of the liquid down prior to entering the vessel 45. In some embodiments, the pressure drop vessel would be maintained above fifty Torr at intermediate pressures such 700 Torr, 500 Torr, 400 Torr, 200 Torr, 100 Torr, 75 Torr, or the like.

In another embodiment (FIG. 5B), liquid enters vessel and is collected in trough 98. Once trough 98 has filled, liquid will pour over the trough and sheet down the sidewalls 105 toward sump 49. The trough 98 may fill to a level defined by a lip 99 until it flows over the lip 99 forming a sheet of liquid across the vessel wall 105. Alternatively, the trough may also contain a gap at the junction with the sidewall resulting in a 'leaky' trough that would result in a uniform sheet of liquid forming along the sidewall as it drains from the bottom of the trough.

Vessel 25 may be constructed of metal, such as stainless steel, copper or aluminum, or plastic, such as polycarbonate or PETG, or a combination thereof. The liquid may directly contact the inner wall 105 of the vessel 45, or may contact a surface liner disposed within and either isolated from, or disposed against the vessel wall 105.

A water jacket 50 may be constructed of a bulk volume between the inner vessel wall and a partially encapsulating wall defining a single thermal zone, or may comprise multiple thermal zones. Multi-zone cooling may be fabricated through the use of bulkheads or pillow plate in the case of stainless steel.

The inner wall 105 of the vacuum chamber 45 may be smooth or even polished, or may be deliberately etched and roughened to promote the evolution of bubbles. A smooth vessel wall 105 will promote liquid flow during helical circulation, while a rough or etched surface may retard liquid flow and result in increased liquid retention times in the case of liquid following a gravitational trajectory along the vessel wall 105.

In another embodiment of the present disclosure, liquid flow is introduced uninterrupted from the inlet port 30 to the liquid sump 49 without contacting the vessel wall 105. In this case the liquid passes or falls straight through the vessel 45 unimpeded and is outgassed during decent.

In still another embodiment (see FIGS. 6A and 6B), pressure vessel 25 has the form of spiral tube, with liquid inlet and gas outlet ports at a first, typically elevated, end 107 and the liquid outlet 40 positioned at the opposite end 109. Liquid typically travels from one end 107 to the other 109 as urged by gravity. In operation, a predetermined quantity of an alcoholic composition 115, such as beer (typically prior to carbonation), wine, liquor, or the like is inlet into pressure chamber 45. Typically, the alcoholic composition 115 enjoys a high surface area-to-volume ratio during residence in the pressure chamber 45, such as in the form of droplets or a thin sheet or ribbon, so that predetermined undesired congeners 120 may be more quickly and efficiently evolved therefrom. The atmosphere in the pressure chamber 45 is below atmospheric pressure (i.e., is a partial vacuum) to encourage the preferential evolution of one or more unwanted congeners 120 from the solution 115. In the case of a batch treatment, the liquid alcoholic composition 115 is loaded into the pressure chamber 45, the pressure chamber 45 is sealed pressure tight, and the pressure therein is reduced to the desired partial vacuum pressure. In the case of continuous flow treatment, the pressure within the pressure chamber 45 is maintained at the desired partial vacuum pressure and the alcoholic composition 115 is flowed therethrough at a predetermined desired rate.

In some embodiments, the ethyl acetate rapidly establishes in thin layers of solution with a thickness between the vessel wall and the vessel atmosphere of less than 25 mm, such as less than 15 mm, less than 10 mm, or less than 5 mm thick.

In some embodiments, residence time at the target atmospheric pressure for the alcoholic composition in the pressure vessel is no more than about sixty seconds, no more than about twenty seconds, or no more than about five seconds. In some embodiments, residence time at the target atmospheric pressure for the alcoholic composition in the pressure vessel is from five to sixty seconds, such as from five to ten seconds, from five to fifteen seconds, from five to twenty seconds, from ten to fifty seconds, from ten to forty seconds, from ten to thirty seconds, from fifteen to thirty seconds, from fifteen to twenty-five seconds, or from fifteen to twenty seconds.

In some embodiments, residence time at the target atmospheric pressure for flowing alcoholic composition 115 is no more than about sixty seconds, no more than about twenty seconds, or no more than about five seconds. In the case of the batch style assembly apparatus, residence time for the alcoholic composition 115 under vacuum may be longer. Moreover, as the vacuum partial pressure decreases, residence time of the alcoholic composition 115 may likewise decrease.

In some embodiments, the temperature of the liquid sample in the pressure chamber may be maintained at, for example, from negative twenty degrees Celsius to eighty degrees Celsius, such as from zero degrees Celsius to sixty degrees Celsius, from ten degrees Celsius to thirty-five degrees Celsius, twenty degrees Celsius to thirty degrees Celsius, or twenty degrees Celsius to twenty-five degrees Celsius. For example, in some embodiments, the temperature of the liquid sample in the pressure chamber may be twenty-one degrees Celsius, twenty-two degrees Celsius, twenty-three degrees Celsius, twenty-four degrees Celsius, or twenty-five degrees Celsius.

In some embodiments, the temperature of the pressure chamber may be maintained at, for example, from negative twenty degrees Celsius to eighty degrees Celsius, such as from zero degrees Celsius to sixty degrees Celsius, from ten degrees Celsius to thirty-five degrees Celsius, twenty degrees Celsius to thirty degrees Celsius, or twenty degrees Celsius to twenty-five degrees Celsius. For example, in some embodiments, the temperature of the pressure chamber may be twenty-one degrees Celsius, twenty-two degrees Celsius, twenty-three degrees Celsius, twenty-four degrees Celsius, or twenty-five degrees Celsius. In some embodiments, the temperature of the pressure chamber is maintained (e.g., at any of the foregoing temperatures) using a jacket or like temperature controller at least partially enveloping the pressure chamber and in thermal communication with the pressure chamber. In some embodiments, said jacket is a water jacket. In some embodiments, the temperature of the liquid sample in the pressure chamber is the same as the temperature at which the pressure chamber is maintained. In some embodiments, the temperature of the liquid sample in the pressure chamber is the different from the temperature at which the pressure chamber is maintained. Thus, in some embodiments, a temperature gradient may exist between the temperature of the pressure chamber (e.g., the temperature in the jacket or like temperature controller) and the temperature of the liquid sample in the pressure chamber.

In some embodiments, the alcoholic composition 115 remains liquid throughout the vacuum treatment process and throughout exposure to the reduced pressure environment in the pressure chamber 45. While the evolved congeners 120 change phase from liquid to gas the alcoholic composition remains liquid, meaning that there is no distillation and/or recondensation or reconstitution of the alcoholic composition 115 during processing in the pressure chamber.

The present disclosure takes advantage of complex intermolecular forces in fermented liquids at low temperatures and pressures to preferentially evolve one or more unwanted congeners from a solution. For example, conventionally, one would expect acetaldehyde to be removed under vacuum before ethyl acetate due to acetaldehyde's higher vapor pressure and lower boiling point at standard temperature and pressure (STP). In fact, in embodiments of methods disclosed herein, amounts of acetaldehyde and isobutanol remain relatively unchanged in the present system while ethyl acetate is selectively removed, which cannot be understood by simply comparing boiling points and vapor pressures. The present method enables the selective control over the amount of ethyl acetate removed based on the temperature and vacuum pressure for a given retention time. This selectivity occurs over a narrow pressure range. As a result, artisans may reliably tune the level of ethyl acetate in alcoholic beverages to create a desired flavor profile. Aspects of this disclosure relate to the removal of ethyl acetate, but other undesirable congeners may be similarly removed by advantageous selection of the pressure and temperature conditions of the vacuum treatment.

Figure 8:
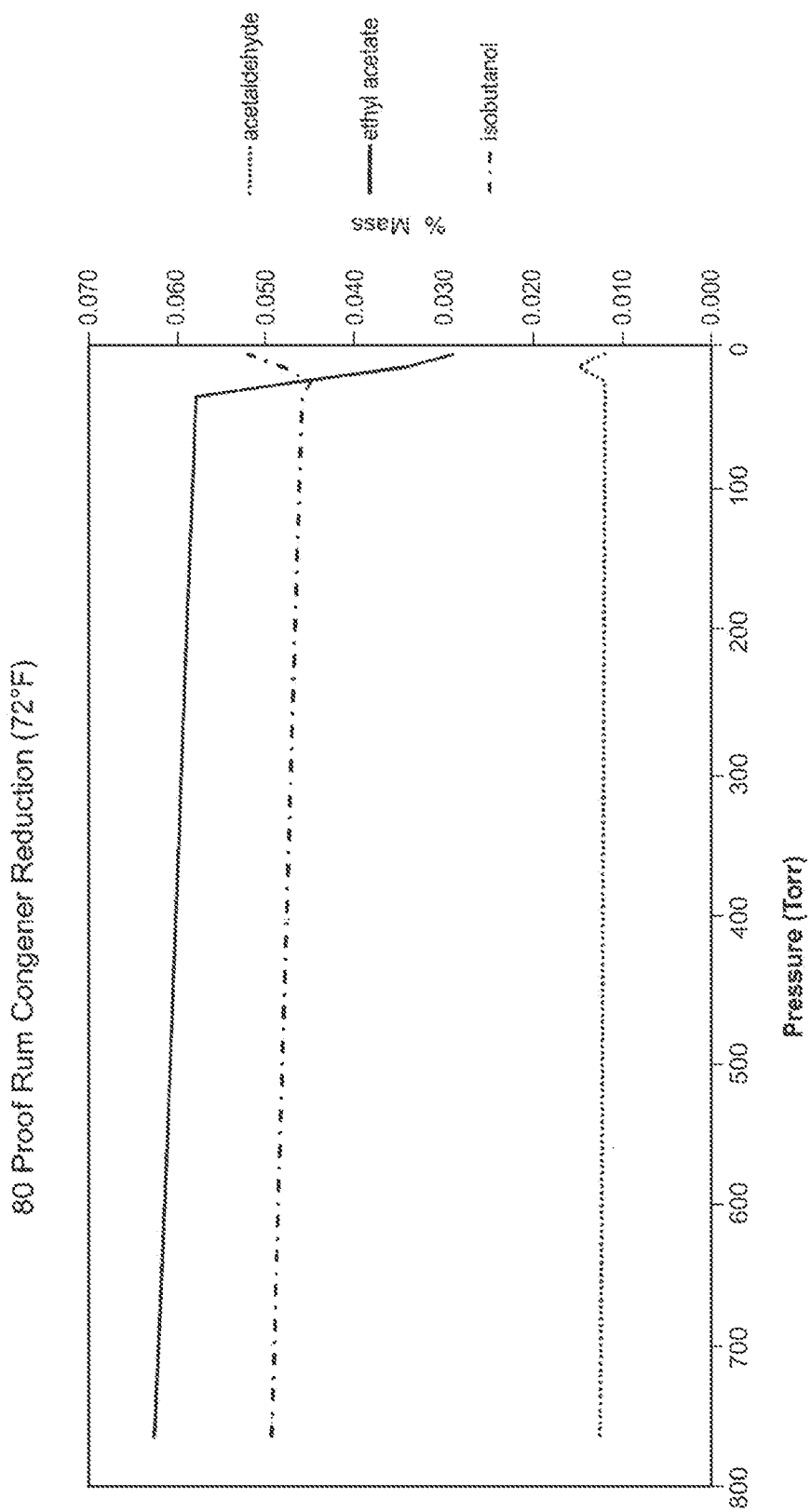
FIG. 8 is a graph of mass percent of congeners as a function of treatment pressure for an alcoholic composition (rum).
Figure 9:
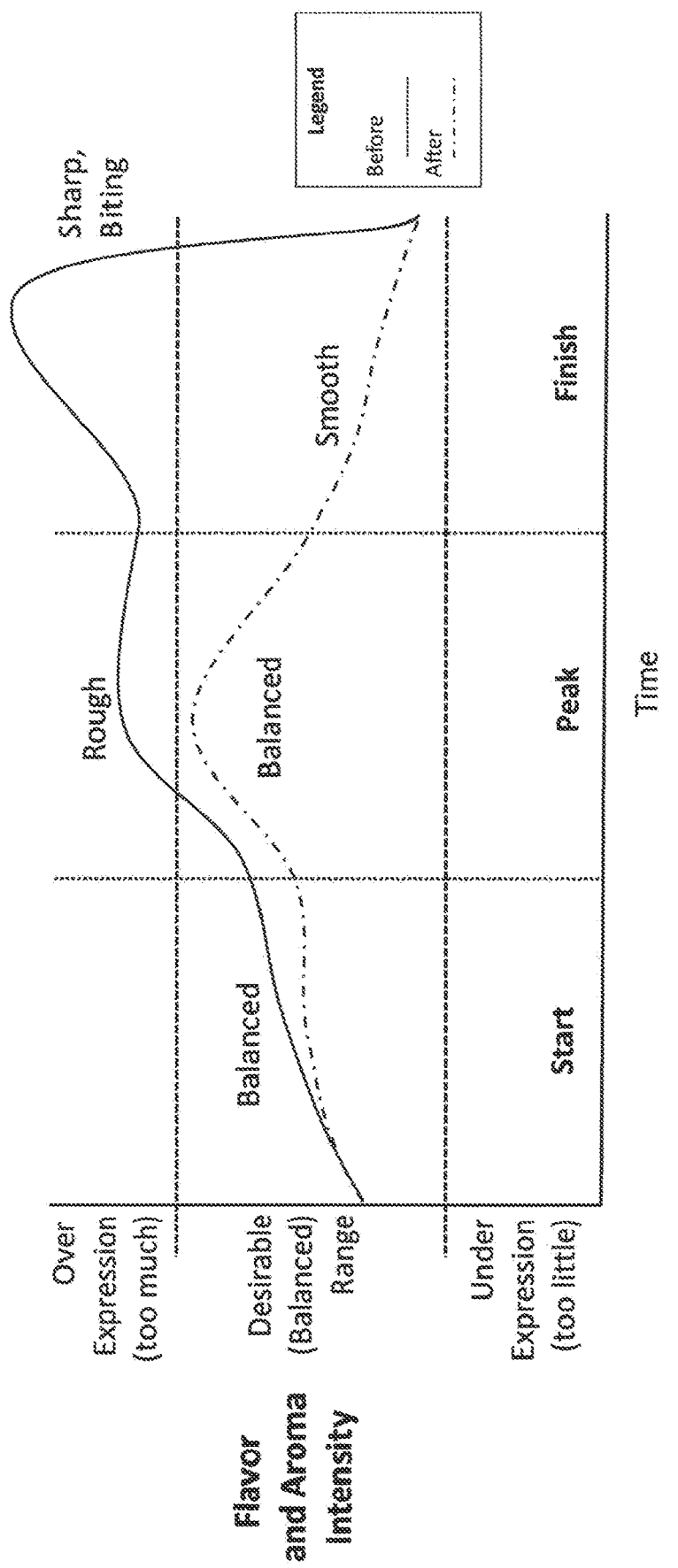
FIG. 9 graphically illustrates the organoleptic property of flavor balancing in terms of flavor/aroma intensity as a function of time.

This evolution of undesirable congeners takes advantage of the fact that while such congeners have boiling points quite close to ethanol at atmospheric pressure, the same congeners have boiling points substantially different from, and typically lower than, ethanol at reduced pressures and the presence of multiple congeners in solution effects the relative boiling points of the other congeners. Thus, exposure of the alcoholic composition to reduced pressures (partial vacuums) at particular temperature and pressure ranges allows for the preferential evolution of certain congeners, such as ethyl acetate, leaving behind the ethanol with certain desired lower boiling point congeners still in solution therewith. For example, FIG. 8 depicts results of an experiment wherein the pressure applied to an 80-proof sample of rum was varied and the mass percentage of acetaldehyde, ethyl acetate, and isobutanol were measured. As shown in FIG. 8, as the pressure was decreased (i.e., as an increasing degree of vacuum was applied), the mass percentage of ethyl acetate decreased, with a precipitous decrease occurring as the pressure was decreased below 100 Torr. In contrast, the mass percentages of isobutanol and acetaldehyde remained steady as the pressure was decreased and did not exhibit the precipitous decrease occurring as the pressure was decreased below 100 Torr observed for ethyl acetate. These results are surprising and unexpected: as discussed above, conventionally, it would be expected that, when an alcoholic composition containing (at least) acetaldehyde and ethyl acetate is exposed to vacuum, acetaldehyde would be preferentially removed relative to ethyl acetate because acetaldehyde has a higher vapor pressure and lower boiling point (at STP) relative to ethyl acetate. Instead, FIG. 8 depicts the opposite result (preferential evolution of ethyl acetate over acetaldehyde). The apparent increase in mass percent acetaldehyde and isobutanol is, without wishing to be bound by theory, believed to be an analytical artifact resulting from the precipitous decrease in the ethyl acetate mass percent and, without wishing to be bound by theory, is not believed to reflect physical reality.

Figure 10:
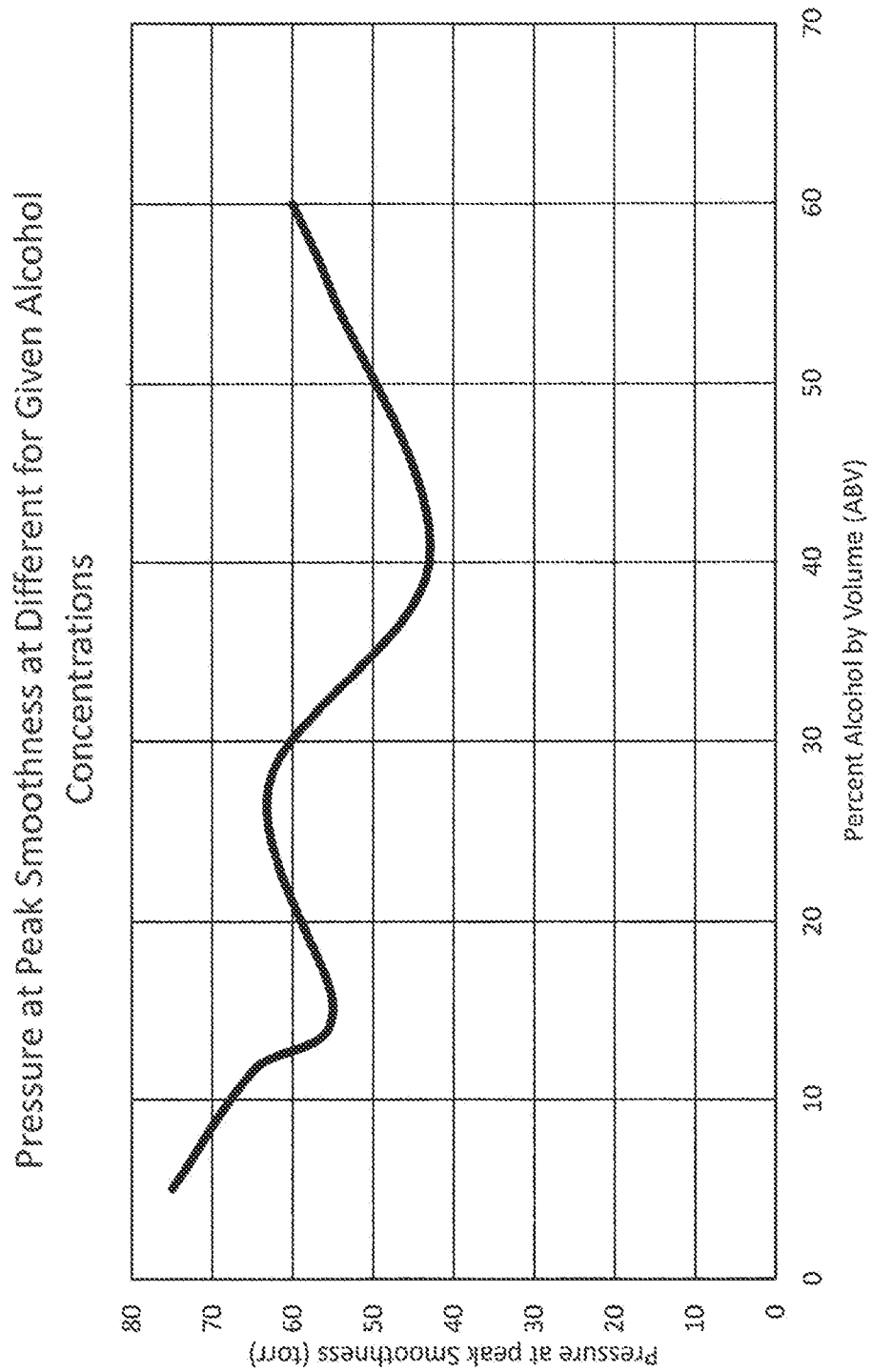
FIG. 10 graphically illustrates peak smoothness of an alcohol with treatment pressure as a function of ethanol content.

By maintaining the atmosphere in the pressure chamber at ambient temperature and at a reduced pressure, ethyl acetate may be partially removed from an alcoholic composition 115 by reestablishing the ethyl acetate equilibrium in the solution resulting in a smooth, organoleptically improved beverage without substantially decreasing the ethanol content of said solution 115. As a non-limiting example, the operating pressure in the pressure chamber at ambient temperature may be maintained at 90 Torr to 15 Torr at 22° C. for a 40% alcohol by volume beverage, such as at 65 Torr to 15 Torr, 55 Torr to 35 Torr, 45 Torr to 40 Torr, or 42 Torr. In some embodiments, the operating pressure in the pressure chamber is a pressure that, for a given composition, has been determined to yield an organoleptically optimized alcoholic beverage or is a multiple of that pressure. In some embodiments, the pressure that has been determined to yield an organoleptically optimized alcoholic beverage is referred to as the pressure that results in "peak smoothness." FIG. 10 depicts a graph of exemplary pressures corresponding to peak smoothness as a function of percent alcohol by volume. In some embodiments, the operating pressure is approximately 0.5 to 2 times the pressure corresponding to peak smoothness, with reference to FIG. 10, such as from 1 to 1.5 times the pressure corresponding to peak smoothness. For example, the operating pressure may be 42 to 63 Torr for an 40% ABV alcoholic composition.

Without wishing to be bound by theory, it is believed that the ability to improve the organoleptic properties of a beverage by exposing it to reduced pressure (e.g., by exposing it to a pressure determined to yield peak smoothness) may result from the fact that ethyl acetate and ethanol have similar boiling points at atmospheric pressure but dissimilar boiling points at pressures from, for example, 20 Torr to 55 Torr for 40% by volume alcoholic compositions, with ethyl acetate having the lower boiling point. Thus, by maintaining a pressure of from 20 Torr to 55 Torr in the pressure chamber 45 and controlling the temperature within the pressure chamber to be about 22° C., the ethyl acetate equilibrium concentration may be preferentially shifted for a 40 percent by volume alcoholic composition.

As shown in FIG. 10, the pressure range at which ethyl acetate may, in some embodiments, be selectively removed (e.g., to provide an organoleptically improved beverage) may shift non-linearly as the alcohol content of the solution shifts. Without wishing to be bound by theory, it is believed that the pressure treatment to yield peak smoothness of the alcohol is a function of alcohol content and, to a lesser extent, congener composition, of the alcohol to be treated. This relationship is nonlinear. For beverages at room temperature with alcohol contents between twenty-four and thirty volume percent, a treatment pressure of between fifty-eight (58) and sixty-seven (67) Torr may yield the smoothest, most organoleptically balanced and positive beverage. For beverages having an alcohol content of between fifty-five and sixty-five volume percent alcohol, a treatment pressure of between forty-nine (49) and fifty-seven Torr may yield the smoothest, most organoleptically balanced and positive beverage. And as noted above, for beverages having forty volume percent alcohol, a pressure treatment forty (40) to forty-five (45) Torr may yield the smoothest, most organoleptically balanced and positive beverage. In some embodiments, pressure treatments hold nominal pressure for five seconds.

Without wishing to be bound by theory, it is believed the ambient liquid environment has an effect on the pressure range under which a given compound (in these examples, ethyl acetate) is selectively removed. In an alcohol vapor environment, the selective pressure range (e.g., about 18 Torr to 55 Torr) may be lower than the range required to achieve an equivalent equilibrium shift of ethyl acetate concentration from another liquid and higher than required to achieve an equivalent equilibrium shift of ethyl acetate from still another liquid.

Figure 11:
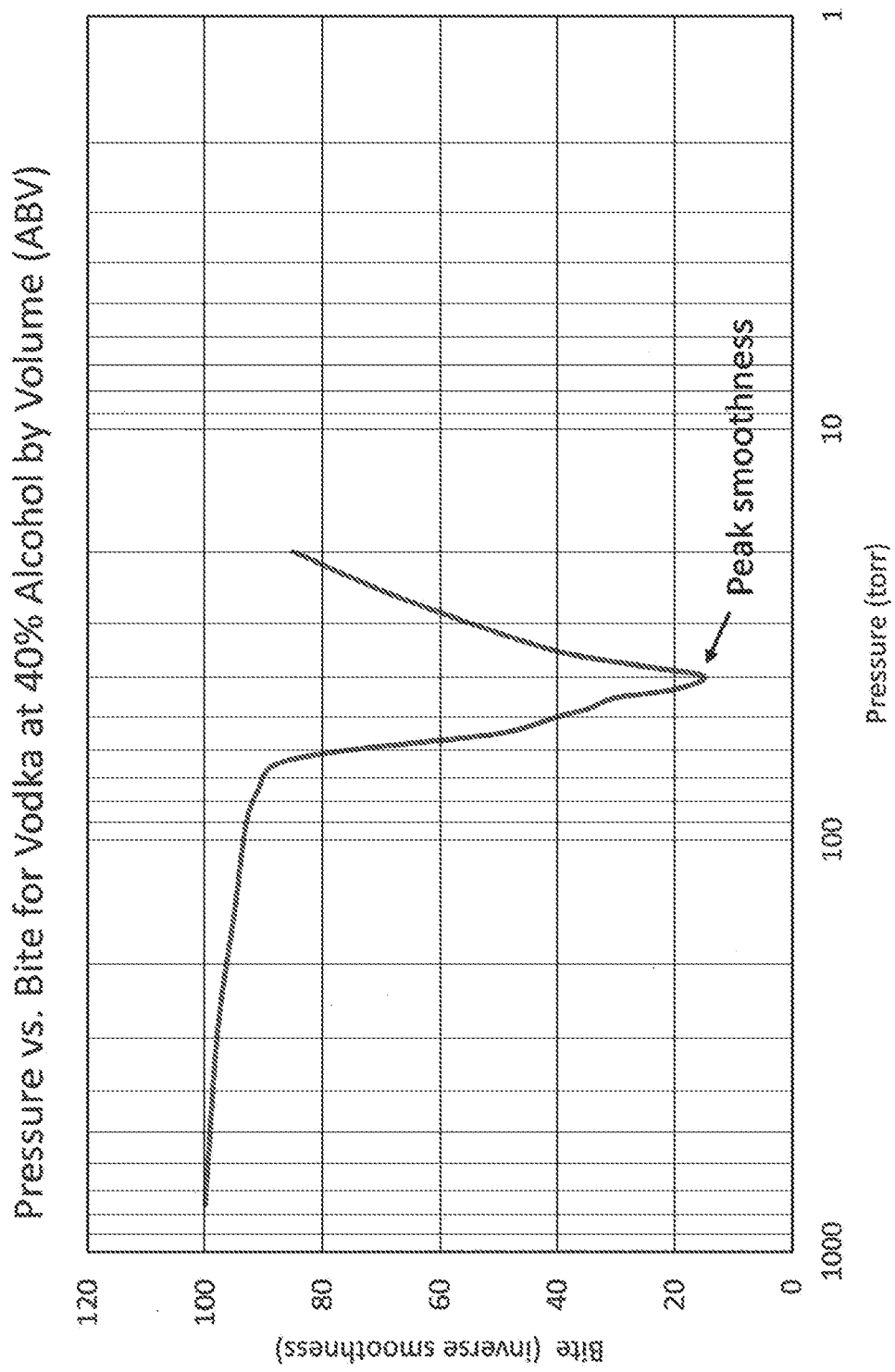
FIG. 11 graphically illustrates bite as a function of treatment pressure for an 80-proof alcoholic composition (vodka).

As depicted in FIG. 11, the relationship between the pressure at which a sample of 40% alcohol by volume vodka is treated and the "bite" (an organoleptic property that is the inverse of "smoothness") is non-linear. In other words, the bite of the treated alcoholic composition decreases with decreasing operating pressure to a point, but, when the operating pressure is further decreased, the bite begins to increase again.

The following example further demonstrates the selective evolution of ethyl acetate from alcoholic compositions achieved through use of processes disclosed herein. In an experiment, a sample of rum was exposed to atmospheric pressure (760 Torr) followed by a series of reduced pressures. In the experiment, the pressure was measured in the vacuum line at a point in fluid communication with the vacuum chamber but, nevertheless, distal to the vacuum chamber. Without wishing to be bound by theory, it is believed that the pressure in the vacuum chamber was higher than the pressure measured. After exposure to atmospheric pressure and each reduced pressure, the ethanolic fraction of the sample was analyzed by gas chromatography-mass spectrometry and the amounts (in area percentages, referred to herein as "A %") of seven analytes (acetaldehyde, ethyl acetate, ethanol, isobutanol, 2-methyl-1-butanol, acetic acid, and furfural) were measured. An additional unknown analyte was also detected and quantified. In the analysis, gas chromatography was performed using a Stabilwax column (Restek), 30 m×0.25 mm ID, 0.25 μm film. The gas chromatography temperature program was 35° C. held for 3 min, ramped to 240° C. at 10° C./min. 0.5 μL of sample was injected with a split of 50:1. Mass spectra data were obtained using an Agilent 5975 C MSD. The results are tabulated in Table 1. The amounts of ethyl acetate are also reported as parts per million (ppm). In this example, to determine the amounts of ethyl acetate (in ppm) in the rum samples, a calibration curve was first generated by analyzing samples of known ethyl acetate concentrations (in ppm) using the same gas chromatograph-mass spectrometry method described above, including measuring peak areas for those samples of known ethyl acetate concentrations (in ppm). The calibration curve provided a correlation between peak area and ethyl acetate concentration (in ppm). The ethyl acetate concentration (in ppm) in the rum samples was then calculated based on the peak area for ethyl acetate in the rum samples by applying the correlation between peak area and ethyl acetate concentration (in ppm) obtained from the calibration curve. For the avoidance of doubt, it is to be understood that the measurements neglect the water content of the sample.

TABLE 1

Amounts of Components Detected in Rum Sample Following Treatment at the Indicated Pressure

| | 760 Torr | 35 Torr | 25 Torr | 15 Torr | 6 Torr |
| --- | --- | --- | --- | --- | --- |
| Acetaldehyde | 0.013 A % | 0.012 A % | 0.012 A % | 0.015 A % | 0.012 A % |
| Ethyl Acetate | 0.063 A % | 0.058 A % | 0.047 A % | 0.034 A % | 0.029 A % |
| | (57.3 ppm) | (33.7 ppm) | (25.9 ppm) | (5.5 ppm) | (3.2 ppm) |
| Ethanol | 98.456 A % | 98.855 A % | 99.218 A % | 99.567 A % | 99.49 A % |
| Isobutanol | 0.05 A % | 0.046 A % | 0.045 A % | 0.048 A % | 0.052 A % |
| 2-Methyl-1-Butanol | 0.312 A % | 0.289 A % | 0.289 A % | 0.28 A % | 0.32 A % |
| Acetic Acid | Not Detected (N.D.) | N.D. | N.D. | N.D. | N.D. |
| Furfural | N.D. | N.D. | N.D. | N.D. | N.D. |
| Unknown | 0.025 A % | 0.021 A % | 0.023 A % | 0.024 A % | 0.024 A % |

Figure 12:
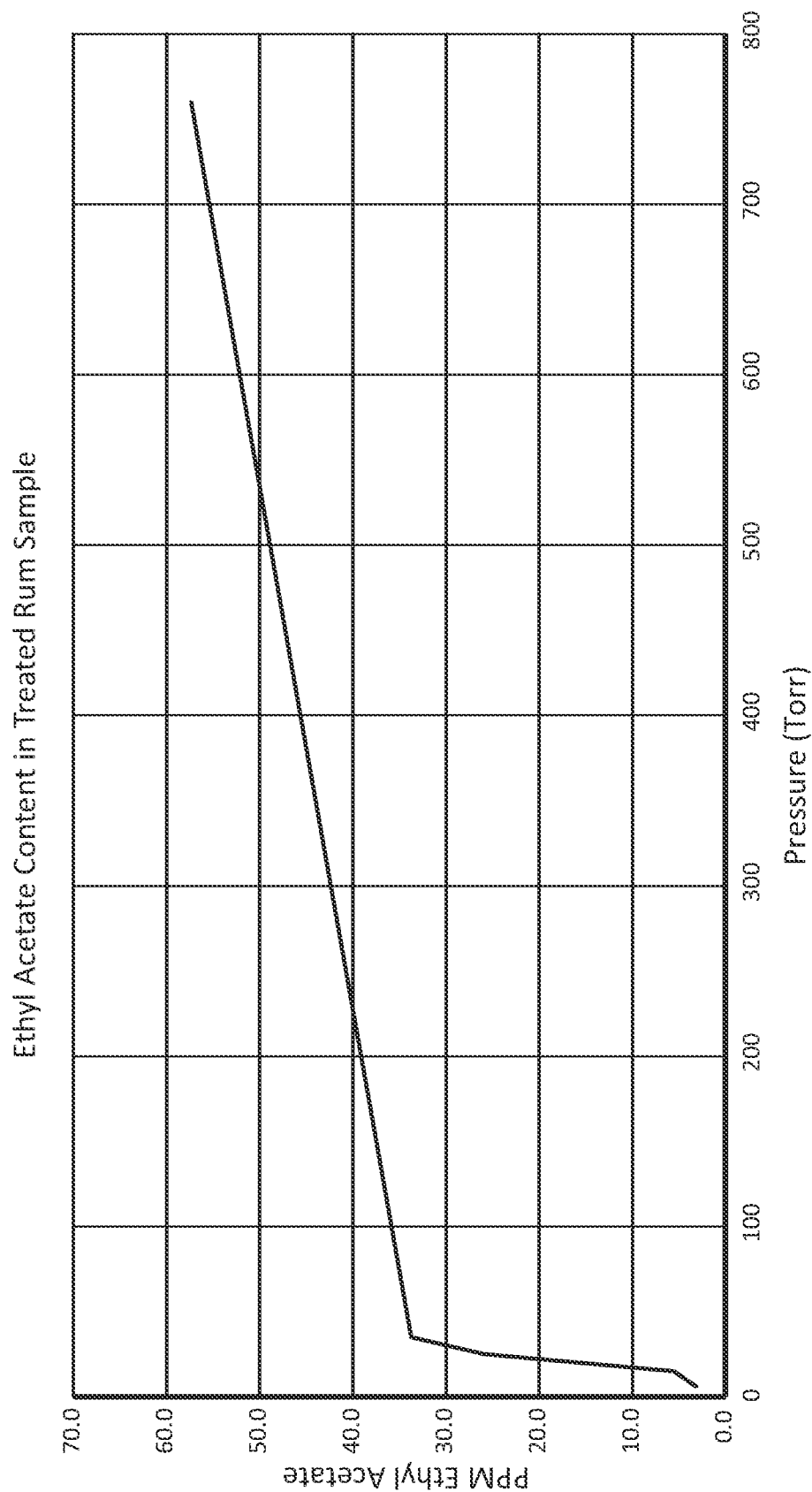
FIG. 12 graphically illustrates an extrapolated relationship between ethyl acetate content in a treated sample of rum and the pressure used for the treatment.

As shown in Table 1, treatment of the rum sample at decreasing pressures resulted in the selective evolution of ethyl acetate while the amounts of, for example, acetaldehyde and ethanol remained approximately constant. As discussed above, this result is surprising and unexpected: conventionally, it would be expected that, when an alcoholic composition containing (at least) acetaldehyde and ethyl acetate is exposed to vacuum, acetaldehyde would be preferentially removed relative to ethyl acetate because acetaldehyde has a higher vapor pressure and lower boiling point (at STP) relative to ethyl acetate. Instead, Table 1 depicts the opposite result (preferential evolution of ethyl acetate over acetaldehyde). Moreover, it is surprising and unexpected that, in some embodiments, it is possible to selectively remove ethyl acetate from a composition containing not only molecules that with lower molecule weights than ethyl acetate but also molecules with higher molecular weights than ethyl acetate by merely adjusting a bulk parameter such as, here, pressure. FIG. 12 is an extrapolated graph of ethyl acetate content (in ppm) versus the treatment pressure and depicts a precipitous decline in ethyl acetate content upon decreasing pressure, particularly below approximately 50 Torr.

In an additional experiment, a sample of bourbon was exposed to atmospheric pressure (760 Torr) followed by two reduced pressures. In the experiment, the pressure was measured in the vacuum line at a point in fluid communication with the vacuum chamber but, nevertheless, distal to the vacuum chamber. Without wishing to be bound by theory, it is believed that the pressure in the vacuum chamber was higher than the pressure measured. After exposure to atmospheric pressure and each reduced pressure, the ethanolic fraction of the sample was analyzed by gas chromatography-mass spectrometry and the amounts of seven analytes (acetaldehyde, ethyl acetate, ethanol, isobutanol, 2-methyl-1-butanol, acetic acid, and furfural) were measured (in area percentages, referred to herein as "A %"). An additional unknown analyte was also detected and quantified. In the analysis, gas chromatography was performed using a Stabilwax column (Restek), 30 m×0.25 mm ID, 0.25 μm film. The gas chromatography temperature program was 35° C. held for 3 min, ramped to 240° C. at 10° C./min. 0.5 μL of sample was injected with a split of 50:1. Mass spectra data were obtained using an Agilent 5975 C MSD. The results are tabulated in Table 2. The amounts of ethyl acetate are also reported as parts per million (ppm). In this example, to determine the amounts of ethyl acetate (in ppm) in the bourbon samples, a calibration curve was first generated by analyzing samples of known ethyl acetate concentrations (in ppm) using the same gas chromatograph-mass spectrometry method described above, including measuring peak areas for those samples of known ethyl acetate concentrations (in ppm). The calibration curve provided a correlation between peak area and ethyl acetate concentration (in ppm). The ethyl acetate concentration (in ppm) in the bourbon samples was then calculated based on the peak area for ethyl acetate in the bourbon samples by applying the correlation between peak area and ethyl acetate concentration (in ppm) obtained from the calibration curve. For the avoidance of doubt, it is to be understood that the measurements neglect the water content of the sample.

TABLE 2

Amounts of Components Detected in Bourbon Sample Following Treatment at the Indicated Pressure

| | 760 Torr | 25 Torr | 6 Torr |
|---|---|---|---|
| Acetaldehyde | 0.003 A % | 0.004 A % | N.D. |
| Ethyl Acetate | 0.143 A % | 0.098 A % | 0.051 A % |
| | (223.0 ppm) | (60.8 ppm) | (20.8 ppm) |
| Ethanol | 99.274 A % | 99.368 A % | 99.386 A % |
| Isobutanol | 0.051 A % | 0.044 A % | 0.044 A % |
| 2-Methyl-1-Butanol | 0.407 A % | 0.366 A % | 0.393 A % |
| Acetic Acid | 0.089 A % | 0.088 A % | 0.1 A % |
| Furfural | 0.004 A % | 0.008 A % | 0.01 A % |
| Unknown | 0.011 A % | 0.009 A % | 0.013 A % |

Figure 13:
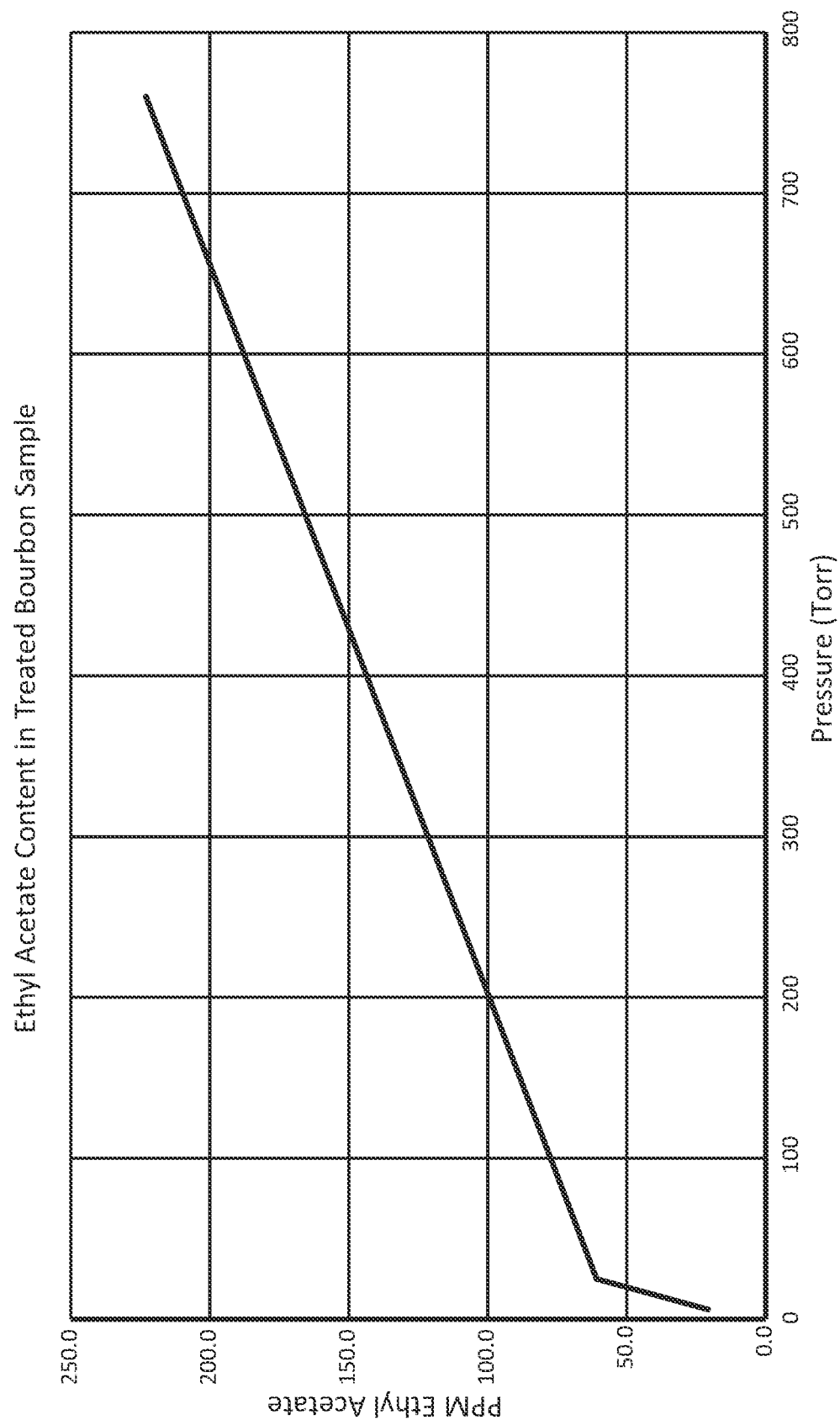
FIG. 13 graphically illustrates an extrapolated relationship between ethyl acetate content in a treated sample of bourbon and the pressure used for the treatment.

As shown in Table 2, treatment of the bourbon sample at decreasing pressures resulted in the selective evolution of ethyl acetate while the amounts of, for example, acetaldehyde and ethanol remained approximately constant. As discussed above, this result is surprising and unexpected: conventionally, it would be expected that, when an alcoholic composition containing (at least) acetaldehyde and ethyl acetate is exposed to vacuum, acetaldehyde would be preferentially removed relative to ethyl acetate because acetaldehyde has a higher vapor pressure and lower boiling point (at STP) relative to ethyl acetate. Instead, Table 2 depicts the opposite result (preferential evolution of ethyl acetate over acetaldehyde). Moreover, it is surprising and unexpected that, in some embodiments, it is possible to selectively remove ethyl acetate from a composition containing not only molecules that with lower molecule weights than ethyl acetate but also molecules with higher molecular weights than ethyl acetate by merely adjusting a bulk parameter such as, here, pressure. FIG. 13 is an extrapolated graph of ethyl acetate content (in ppm) versus the treatment pressure and depicts a precipitous decline in ethyl acetate content upon decreasing pressure, particularly below approximately 50 Torr.

The effect of reduced pressure treatment on alcoholic compositions may be better understood as a shift of equilibrium concentration of ethyl acetate rather than removal of the same throughout partial distillation. Consequently, solution retention time at reduced pressure may not cause ethyl acetate concentration to drop to zero. The solution might experience a shift in congener concentration for a given retention time. In some embodiments, at least one third of the ethyl acetate is preferentially removed, at least one half is preferentially removed, at least two-thirds are preferentially removed, or substantially all the ethyl acetate is preferentially removed from the alcoholic composition. As used herein, preferentially removing an unwanted congener, such as ethyl acetate, means removing some or all of the unwanted congener from solution without substantially removing some, many, or any of the other constituents of the solution. In an embodiment, at about forty Torr and twenty-two degrees Celsius, between forty and sixty percent of the initial ethyl acetate content is removed in about five seconds from a 40 percent alcohol by volume alcoholic composition.

In some embodiments, the instant alcohol rehabilitation treatment reduces the quantity of ethyl acetate in an alcoholic composition to about fifty percent or less of the original ethyl acetate content in the alcoholic composition, such as about 45 percent of the original ethyl acetate content or less, about 40 percent of the original ethyl acetate content or less, about 35 percent of the original ethyl acetate, about 30 percent of the original ethyl acetate content or less, about 20 percent of the original ethyl acetate content or less, about 10 percent of the original ethyl acetate content or less, or about 5 percent of the original ethyl acetate content or less. The target amount of ethyl acetate content reduction is determined by a number of factors, including personal taste and type of alcoholic beverage, which range in ethanol content from 3 volume percent to 95 volume percent. For example, alcoholic beverages may have an ethanol content of 1 to 5 volume percent, 3 to 5 volume percent, 5 to 10 volume percent, 10 to 15 volume percent, 10 to 20 volume percent, 20 to 30 volume percent, 30 to 40 volume percent, 40 to 50 volume percent, 45 to 50 volume percent, 50 to 60 volume percent, 55 to 60, 60 to 70 volume percent, 70 to 80 volume percent, 80 to 90 volume percent, or 90 to 95 volume percent. In some embodiments, the ethyl acetate content of an alcoholic composition is reduced to <1%, 1%, 2%, 3%, 4%, 5%, 6%, 7%, 8%, 9%, 10%, 15%, 20%, 25%, 30%, 33⅓% (i.e., one-third), 35%, 40%, 45%, 50% (i.e., half), 55%, 60%, 65%, 66⅔% (i.e., two-thirds), 70%, 75%, 80%, 85%, 90%, 95%, or 99% of the original content. In some embodiments, the ethyl acetate content of an alcoholic composition is reduced to from 20% to 80% of the original content, such as from 25% to 75% of the original content or from 33⅓% to 66⅔%. In some embodiments, including, but not limited to, embodiments described in this paragraph, the reduction in the ethyl acetate content of an alcoholic composition is measured using liquid phase gas chromatography-mass spectrometry.

In some embodiments, the methods disclosed herein may be applied to reduce the ethyl acetate content of an alcoholic composition, as measured by liquid phase gas chromatography-mass spectrometry to, for example, from 1 ppm to 400 ppm, such as from 1 ppm to 350 ppm, from 1 ppm to 300 ppm, from 1 ppm to 250 ppm, from 1 ppm to 200 ppm, from 1 ppm to 150 ppm, from 1 ppm to 100 ppm, from 1 ppm to 75 ppm, from 1 ppm to 50 ppm, or from 1 ppm to 25 ppm. In some embodiments, the methods disclosed herein may be applied to reduce the ethyl acetate content of an alcoholic composition, as measured by liquid phase gas chromatography-mass spectrometry to, for example, from 10 ppm to 400 ppm, from 20 ppm to 380 ppm, from 25 ppm to 375 ppm, from 30 ppm to 350 ppm, from 35 ppm to 325 ppm, from 40 ppm to 300 ppm, from 45 ppm to 275 ppm, from 50 ppm to 250 ppm, from 55 ppm to 225 ppm, from 60 ppm to 200 ppm, from 65 ppm to 175 ppm, from 70 ppm to 150 ppm, from 75 ppm to 125 ppm, or from 80 ppm to 100 ppm. In some embodiments, the methods disclosed herein may be applied to reduce the ethyl acetate content of an alcoholic composition, as measured by liquid phase gas chromatography-mass spectrometry to, for example, from 3 ppm to 300 ppm. In some embodiments, the methods disclosed herein may be applied to reduce the ethyl acetate content of an alcoholic composition, as measured by liquid phase gas chromatography-mass spectrometry to, for example, from 3 ppm to 100 ppm, from 3 ppm to 80 ppm, from 3 ppm to 70 ppm, from 3 ppm to 60 ppm, or from 3 ppm to 50 ppm. In some embodiments, the methods disclosed herein may be applied to reduce the ethyl acetate content of an alcoholic composition, as measured by liquid phase gas chromatography-mass spectrometry to, for example, from 15 ppm to 200 ppm.

In some embodiments, for an alcoholic composition with an ethanol content from 40% by volume to 60% by volume, the methods disclosed herein may be applied to reduce the ethyl acetate content of the alcoholic composition, as measured by liquid phase gas chromatography-mass spectrometry to, for example, from 3 ppm to 250 ppm, such as from 5 ppm to 100 ppm, from 10 ppm to 250 ppm, from 20 ppm to 225 ppm, from 10 ppm to 80 ppm, from 3 ppm to 100 ppm, from 5 ppm to 75 ppm, or from 10 ppm to 60 ppm. In some embodiments, the methods disclosed herein may be applied to reduce the ethyl acetate content of the alcoholic composition and thereby provide an alcoholic composition with improved organoleptic properties relative to the starting alcoholic composition. For example, in some embodiments, for an alcoholic composition with an ethanol content from 40% by volume to 60% by volume, the methods disclosed herein may be applied to reduce the ethyl acetate content of the alcoholic composition, as measured by liquid phase gas chromatography-mass spectrometry to, for example, from 5 to 100 ppm and thereby provide an alcoholic composition with improved organoleptic properties relative to the starting alcoholic composition.

In some embodiments, for an alcoholic composition with an ethanol content from 10% by volume to 20% by volume, the methods disclosed herein may be applied to reduce the ethyl acetate content of the alcoholic composition, as measured by liquid phase gas chromatography-mass spectrometry to, for example, from 3 ppm to 200 ppm, such as from 3 ppm to 175 ppm, from 3 ppm to 150 ppm, from 3 ppm to 75 ppm, from 3 ppm to 65 ppm, from 3 ppm to 60 ppm, from 10 ppm to 200 ppm, from 10 ppm to 175 ppm, from 10 ppm to 150 ppm, from 10 ppm to 125 ppm, from 10 ppm to 100 ppm, from 10 ppm to 80 ppm, from 12 ppm to 100 ppm, from 12 ppm to 80 ppm, from 12 ppm to 70 ppm, from 12 ppm to 60 ppm, from 15 ppm to 50 ppm, from 15 ppm to 45 ppm, from 20 ppm to 60 ppm, from 20 ppm to 50 ppm, from 25 ppm to 45 ppm, from 30 ppm to 60 ppm, from 30 ppm to 50 ppm, or from 20 ppm to 40 ppm. In some embodiments, the methods disclosed herein may be applied to reduce the ethyl acetate content of the alcoholic composition and thereby provide an alcoholic composition with improved organoleptic properties relative to the starting alcoholic composition. For example, in some embodiments, for an alcoholic composition with an ethanol content from 10% by volume to 20% by volume, the methods disclosed herein may be applied to reduce the ethyl acetate content of the alcoholic composition, as measured by liquid phase gas chromatography-mass spectrometry to, for example, from 10 to 90 ppm and thereby provide an alcoholic composition with improved organoleptic properties relative to the starting alcoholic composition.

As an additional representative but non-limiting example, the methods disclosed herein may be applied to, for example, a rum sample having an initial content of 55 ppm to 60 ppm ethyl acetate as measured by liquid phase gas chromatography-mass spectrometry to reduce the ethyl acetate content to less than 40 ppm, such as to less than 35 ppm, less than 30 ppm, less than 25 ppm, less than 10 ppm, less than 5 ppm, or less than 4 ppm, each as measured by liquid phase gas chromatography-mass spectrometry. For example, the methods disclosed herein may be applied to a rum sample having an initial content of 55 to 60 ppm ethyl acetate as measured by liquid phase gas chromatography-mass spectrometry to reduce the ethyl acetate content to, for example, 50 ppm to 60 ppm, 25 ppm to 35 ppm, 15 ppm to 25 ppm, 5 ppm to 15 ppm, or 1 ppm to 5 ppm, each as measured by liquid phase gas chromatography-mass spectrometry. As an additional representative but non-limiting example, the methods disclosed herein may be applied to, for example, a bourbon initially having 210 to 230 ppm ethyl acetate as measured by liquid phase gas chromatography-mass spectrometry to reduce the ethyl acetate content to, for example, less than 100 ppm, less than 80 ppm, less than 70 ppm, less than 60 ppm, less than 50 ppm, less than 40 ppm, less than 30 ppm, or less than 25 ppm, each as measured by liquid phase gas chromatography-mass spectrometry. For example, the methods disclosed herein may be applied to a bourbon sample having an initial content of 200 to 250 ppm ethyl acetate as measured by liquid phase gas chromatography-mass spectrometry to reduce the ethyl acetate content to, for example, 50 ppm to 75 ppm, 55 to 65 ppm, 15 ppm to 35 ppm, or 15 ppm to 25 ppm, each as measured by liquid phase gas chromatography-mass spectrometry.

By selecting other treatment temperature/pressure/residence time combinations, other congeners may likewise be selectively removed. In some embodiments, temperature sensors and/or pressure sensors and/or chemical sensors (or combinations of the same) are positioned in thermal communication with the interior of the vessel 25 and/or the water jacket and/or the vapor outlet port (or combinations of the same). These sensors may be operationally connected to an electronic controller that may likewise be connected to one or more of the pumps 60, 75, 85 and/or ports 30, 35, 40 and/or valves 70 and/or agitators 95 (if present) to provide feedback-based control of the process to maintain the process within predetermined parameters and/or within predetermined pressure/temperature profiles. In some embodiments, the temperature and pressure within the chamber may be varied during residence of the alcoholic composition 115 to selectively target and remove a plurality of undesired congeners 120; this technique would likely apply best to a batch treatment. In other embodiments, the alcoholic composition 115 may be flowed sequentially through a plurality of pressure vessels 25, each having a pressure chamber 45 characterized by a different predetermined vacuum partial pressure and temperature to target one or more specific congeners 120.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. A method for removing ethyl acetate from an alcoholic composition, comprising:
   a) placing a quantity of alcoholic composition in a pressure-controllable environment;
   b) decreasing a pressure of the pressure controllable environment to a pressure between eighty and forty Torr;
   c) holding the pressure of the pressure-controllable environment at between eighty and forty Torr for a first predetermined period of time;
   d) preferentially removing ethyl acetate relative to other congeners of a group of congeners from the alcoholic composition to yield a first purified alcoholic composition; and
   e) removing the first purified alcoholic composition from the pressure controllable environment.

2. The method of claim 1, wherein the alcoholic composition contains from 3% ethanol by volume to 95% ethanol by volume.

3. The method of claim 1, further comprising:
   f) after b) and before e), cooling the pressure controllable environment.

4. The method of claim 1, wherein a temperature of the pressure controllable environment is maintained at from negative twenty degrees Celsius to eighty degrees Celsius.

5. The method of claim 1, wherein a temperature of the pressure controllable environment is maintained at from ten degrees Celsius to thirty five degrees Celsius.

6. The method of claim 1, wherein the first predetermined period of time is 5 seconds.

7. The method of claim 1, wherein an ethyl acetate concentration of the first purified alcoholic composition is one-third, one-half, or two-thirds of an ethyl acetate concentration of the alcoholic composition.

8. The method of claim 1, wherein an ethyl acetate concentration of the first purified alcoholic composition is about one-third of an ethyl acetate concentration of the alcoholic composition.

9. The method of claim 1, wherein the first purified alcoholic composition has an ethyl acetate concentration that is from 1 ppm to 400 ppm as measured by liquid phase gas chromatography-mass spectrometry.

10. The method of claim 1, wherein the first purified alcoholic composition has an ethyl acetate concentration that is from 5 ppm to 300 ppm as measured by liquid phase gas chromatography-mass spectrometry.

11. The method of claim 1, further comprising:
    g) removing one or more further congeners from the first purified alcoholic composition to yield a second purified alcoholic composition.

12. The method of claim 1, wherein the pressure controllable environment further comprises:
    a pressure vessel defining a pressure controllable chamber;
    a jacket at least partially surrounding the pressure controllable chamber and in thermal communication therewith;
    a liquid inlet port in fluidic communication with the pressure controllable chamber;
    a gas outlet port in fluidic communication with the pressure controllable chamber;
    a vacuum pump in fluidic communication with the gas outlet port;
    a collection vessel; and
    a liquid outlet port in fluidic communication with the pressure controllable chamber.

13. The method of claim 12, wherein the jacket is a water jacket.

14. The method of claim 1, wherein during b), the pressure of the pressure-controllable environment is decreased to a pressure of forty-two Torr; and wherein during c) the pressure-controllable environment is maintained at a pressure of forty-two Torr.

15. A method for removing ethyl acetate from an alcoholic composition, comprising:
    a) establishing a partial vacuum in a pressure vessel;
    b) flowing a quantity of alcoholic composition into the pressure vessel;
    c) at least partially preferentially removing ethyl acetate relative to acetaldehyde or ethanol from the alcoholic composition to yield a purified alcoholic composition; and
    d) extracting the purified alcoholic composition from the pressure vessel;
    wherein, while in the pressure vessel, the alcoholic composition remains liquid.

16. The method of claim 15, wherein:
the partial vacuum ranges from 15 Torr to 90 Torr; and
c) is performed at a temperature from ten to thirty-five degrees Celsius for from five to sixty seconds.

17. The method of claim 15, wherein:
the partial vacuum is about 42 Torr; and
c) is performed at about 22 degrees Celsius for about 5 seconds.

18. A method for removing ethyl acetate from an alcohol composition, comprising:
a) placing a quantity of an unpurified aqueous solution of alcohol in a pressure and temperature-controllable environment;
b) decreasing a pressure of the pressure and temperature-controllable environment to a pressure between eighty and twenty Torr;
c) holding the pressure of the pressure and temperature-controllable environment at between eighty and twenty Torr for a first predetermined period of time;
d) preferentially removing ethyl acetate relative to molecules with different molecular weights than the ethyl acetate from the unpurified aqueous solution of alcohol to yield a first purified aqueous solution of alcohol; and
e) removing the first purified aqueous solution of alcohol from the pressure and temperature-controllable environment;
wherein the first purified aqueous solution of alcohol has substantially the same composition as the unpurified aqueous solution of alcohol with the exception being that the first purified aqueous solution of alcohol contains substantially less ethyl acetate than the unpurified aqueous solution of alcohol, and
wherein during c), a temperature within the pressure and temperature-controllable environment is controlled such that substantially only ethyl acetate is removed from the unpurified aqueous solution in the pressure and temperature-controllable environment.

19. The method of claim 18 wherein during c), the pressure within the pressure and temperature-controllable environment is maintained between twenty Torr and eighty Torr and the temperature within the pressure and temperature-controllable environment is maintained at twenty-two degrees Celsius.

20. A method for selectively removing ethyl acetate from an alcoholic composition, comprising:
a) establishing a partial vacuum in a pressure vessel;
b) flowing a quantity of alcoholic composition into the pressure vessel wherein the alcoholic composition is further comprised of a plurality of components, one of which is ethyl acetate;
c) at least partially preferentially removing ethyl acetate relative to congeners with higher vapor pressure and lower boiling point than ethyl acetate from the alcoholic composition to yield a purified alcoholic composition; and
d) extracting the purified alcoholic composition from the pressure vessel,
wherein, while in the pressure vessel, the alcoholic composition remains liquid, and
wherein temperature and pressure conditions within the pressure vessel permit selectively removing ethyl acetate from the alcoholic composition without substantially decreasing relative concentration of any remaining component.

21. The method of claim 20 wherein the alcoholic composition is an aqueous ethanol solution.

22. The method of claim 1, wherein preferentially removing ethyl acetate includes removing the other congeners of the group of congeners comprising acetaldehyde, ethanol, isobutanol, 2-methyl-1-butanol, acetic acid, or furfural.

23. The method of claim 18, wherein preferentially removing ethyl acetate includes preferentially removing ethyl acetate relative to molecules with lower molecular weights than ethyl acetate.

24. The method of claim 18, wherein preferentially removing ethyl acetate includes preferentially removing ethyl acetate relative to molecules with higher molecular weights than ethyl acetate.

25. The method of claim 20, wherein selectively removing ethyl acetate from the alcoholic composition without substantially decreasing relative concentration of any remaining component includes maintaining relative concentration of acetaldehyde or ethanol.

* * * * *